US009619771B2

(12) United States Patent
Rao et al.

(10) Patent No.: US 9,619,771 B2
(45) Date of Patent: Apr. 11, 2017

(54) SYSTEMS AND METHODS FOR DIGITAL WORKFLOW AND COMMUNICATION

(71) Applicant: Wearable Intelligence, Inc., San Francisco, CA (US)

(72) Inventors: Raghav Rao, Fremont, CA (US); Peter Bisroev, New York, NY (US); Yan-David Erlich, San Francisco, CA (US); Ryan Alexander Junee, San Francisco, CA (US)

(73) Assignee: Parsable, Inc., San Francisco, CA (US)

( * ) Notice: Subject to any disclaimer, the term of this patent is extended or adjusted under 35 U.S.C. 154(b) by 0 days.

(21) Appl. No.: 14/679,958

(22) Filed: Apr. 6, 2015

(65) Prior Publication Data

US 2015/0288666 A1    Oct. 8, 2015

Related U.S. Application Data

(60) Provisional application No. 61/975,800, filed on Apr. 5, 2014.

(51) Int. Cl.
*H04L 29/06* (2006.01)
*G06Q 10/06* (2012.01)
(Continued)

(52) U.S. Cl.
CPC ..... *G06Q 10/06316* (2013.01); *G06F 3/0481* (2013.01); *G06F 17/2247* (2013.01);
(Continued)

(58) Field of Classification Search
None
See application file for complete search history.

(56) References Cited

U.S. PATENT DOCUMENTS 6,643,781 B1 * 11/2003 Merriam ............... G06F 21/88
380/211
2004/0098583 A1 * 5/2004 Weber ............... H04L 63/0492
713/168

(Continued)

FOREIGN PATENT DOCUMENTS

EP    2693687 A1    2/2014

OTHER PUBLICATIONS

Alexandre Alapetite (Apr. 2, 2009) "Dynamic 2D-barcodes for multi-device Web session migration including mobile phones", *Personal and Ubiquitous Computing*, 14(1), pp. 45-52.

(Continued)

*Primary Examiner* — Shin-Hon Chen
(74) *Attorney, Agent, or Firm* — Goodwin Procter LLP

(57) ABSTRACT

Systems and methods for authoring and performing procedural workflows, and engaging in multimedia communication, remote assistance, training, data entry, inventory management, authentication, and secure networking using a hands-free or substantially hands-free wearable digital device are described. In one implementation, a user logs into a secure network using existing credentials, and a Quick Response Code is generated to temporarily authorize the user's wearable device within the secure network. In another implementation, information is encrypted and transferred between a computing device and a remote system, and the computing device is verified as being connected to a particular network and located within a particular geofence. In a further implementation, an interface for authoring a procedural workflow includes defining workflow steps based on selected primitives, and displaying rendered previews of the workflow as it would appear on different user devices.

12 Claims, 34 Drawing Sheets

(51) Int. Cl.
*G06F 3/0481* (2013.01)
*G06F 17/22* (2006.01)
*H04L 29/08* (2006.01)
*H04L 9/32* (2006.01)
*G06F 7/04* (2006.01)
*G06F 15/16* (2006.01)
*G06F 17/30* (2006.01)

(52) U.S. Cl.
CPC ........ *H04L 63/0442* (2013.01); *H04L 63/061* (2013.01); *H04L 63/0807* (2013.01); *H04L 63/0846* (2013.01); *H04L 63/0853* (2013.01); *H04L 67/02* (2013.01); *H04L 67/10* (2013.01)

(56) References Cited

U.S. PATENT DOCUMENTS

| | | | | |
|---|---|---|---|---|
| 2007/0268911 | A1* | 11/2007 | Alve | H04L 63/0492 370/395.52 |
| 2010/0017602 | A1* | 1/2010 | Bussard | H04L 9/0844 713/168 |
| 2010/0031029 | A1* | 2/2010 | Ilyadis | H04L 9/3271 713/156 |
| 2012/0088487 | A1* | 4/2012 | Khan | H04W 4/001 455/418 |
| 2012/0172027 | A1* | 7/2012 | Partheesh | H04W 4/021 455/420 |
| 2012/0220307 | A1* | 8/2012 | Wohlert | H04W 4/02 455/456.1 |
| 2012/0226905 | A1* | 9/2012 | Mohanty | H04L 9/0825 713/168 |
| 2013/0045760 | A1* | 2/2013 | Obermeyer | G08B 21/0277 455/456.6 |
| 2013/0104238 | A1* | 4/2013 | Balsan | G06Q 30/0207 726/26 |
| 2013/0124568 | A1* | 5/2013 | Wang | G06F 21/62 707/783 |
| 2013/0124855 | A1 | 5/2013 | Varadarajan et al. | |
| 2013/0219479 | A1 | 8/2013 | DeSoto et al. | |
| 2014/0106710 | A1* | 4/2014 | Rodriguez | H04M 1/7253 455/411 |
| 2014/0282877 | A1* | 9/2014 | Mahaffey | H04L 63/0853 726/3 |
| 2014/0282985 | A1* | 9/2014 | Joseph | G06F 21/34 726/9 |

OTHER PUBLICATIONS

International Search Report and Written Opinion for International Patent Application No. PCT/US2015/024585 mailed Oct. 12, 2015, (16 pages).

Choi, K., et al., (Sep. 26, 2011) "A mobile based anti-phishing authentication scheme using QR code", *Mobile IT Convergence (ICMIC), IEEE*, pp. 109-113.

* cited by examiner

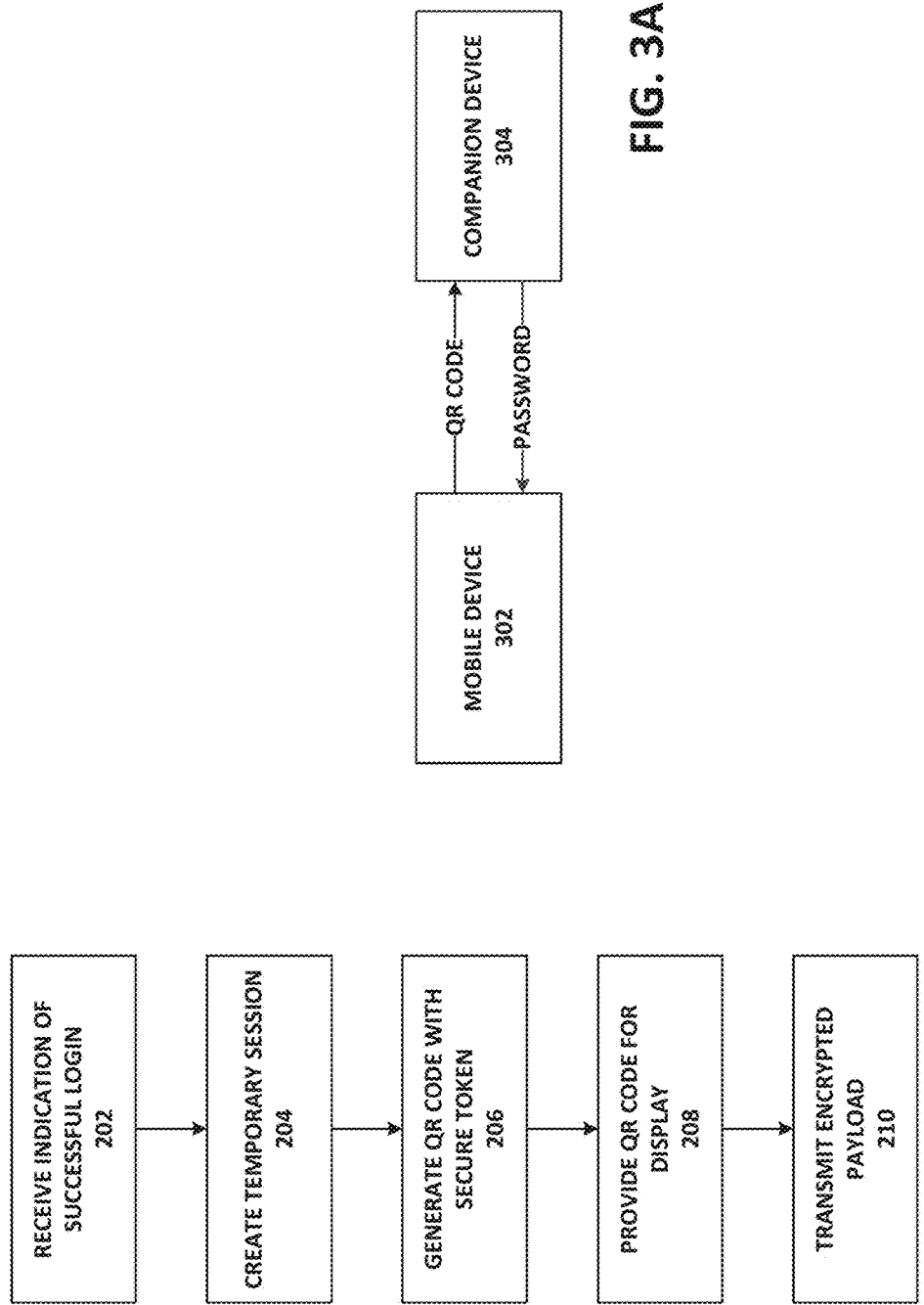

wearable
intelligence

Welcome Tom Hirschfeld! You're logged in as an admin.  [New Standard Work] [Import Standard Work] [Logout]

| Standard Work Name | Type | Version | Author | Created ▼ | Last Updated | Reviewed | Status |
|---|---|---|---|---|---|---|---|
| test c | Checklist | 1.0 | yanda-admin | 3/28/15 7:04PM | 3/28/15 7:36PM | | [Editing] |

Download PDF
View
Change Author

| Step | Value | Time Spent | Status |
|---|---|---|---|
| Step REQUIRED PPE | | | Complete |
| Step REQUIRED PPE | | 35 seconds | Complete |
| Step TABLE | Category / ID <br> Plant / 301 <br> Site / 502354 | 3 seconds | Complete |
| Step 1 What is the job number? | 501.0 | 7 seconds | Complete |
| Step 1 Twist the cables counterclockwise | | 4 seconds | Complete |
| Step ⚠ Did you go through all of the safety requirements before | | 4 seconds | Complete |

FIG. 21C

SYSTEMS AND METHODS FOR DIGITAL WORKFLOW AND COMMUNICATION

CROSS-REFERENCE TO RELATED APPLICATION

This application claims priority to and the benefit of U.S. Provisional Patent Application No. 61/975,800, filed on Apr. 5, 2014, and entitled "Systems and Methods for Digital Workflow and Communication," the entirety of which is incorporated by reference herein.

BACKGROUND

The present disclosure relates generally to procedural workflow and communications and, more particularly, to systems and methods for authoring and engaging in procedural workflows, multimedia communication, remote assistance, training, data entry, inventory management, authentication, data transfer, and secure networking using hands-free or substantially hands-free wearable digital devices.

Onsite workers in industrial, clinical, and other settings routinely perform standard procedures that consist of ordered steps. However, these workers often do not have the information needed to perform these procedures readily available at their fingertips, nor is help easily available when obstacles are encountered. Furthermore, it is difficult to ensure that the workers have properly performed each step in a particular standard procedure, let alone performed the steps in a reasonable amount of time.

BRIEF SUMMARY

Systems and methods for digital procedural workflow authoring and execution, and secure network connectivity and data transfer are described. In one aspect, a method performed by a computing device comprises: receiving an indication that a user has successfully logged into a secure network using existing credentials; creating a temporary session for the user based on the existing credentials; generating a Quick Response (QR) code comprising a secure token associated with the temporary session; and providing the QR code for display to the user on a first device such that the user can scan the QR code and authorize a second device for the temporary session based on the secure token.

In one implementation, generating the temporary session further comprises defining a permitted session length associated with the temporary account. The QR code can further include information associated with the temporary session, the information comprising at least one of permitted session length and a condition for ending the temporary session.

In another implementation, the method further includes transmitting an encrypted payload to the second device. Transmitting the encrypted payload to the second device can include providing a second QR code for scanning by the second device, wherein the second QR code comprises the encrypted payload. The encrypted payload can be generated based on a password provided by the second device.

In another aspect, a method performed by a computing device comprises receiving, at a first device, a password generated by a second device; receiving, at the first device, a message to be transferred to the second device; generating an encrypted payload based on the password and the message; generating a Quick Response (QR) code based on the encrypted payload; and providing the QR code for scanning by the second device.

In one implementation, the password is inputted into the first device by a user of the first device. The password can be a randomly-generated character string. Generating the encrypted payload can include converting the message to a UTF-8 encoded format, padding the message to a fixed length, and/or generating a salt. The salt can be a random initialization vector.

In another implementation, the encrypted payload further includes generating an encryption key based on the password and the salt. Generating the encrypted payload can further include encrypting the message using the encryption key and the salt.

In another aspect, a method performed by a computing device includes: generating a password at a first device; making the password available to a second device; receiving at the first device a Quick Response (QR) code generated by the second device, the QR code comprising an encrypted payload; and decrypting the encrypted payload based at least in part on the password.

In one implementation, decrypting the encrypted payload includes identifying a portion of the payload that comprises a salt. Decrypting the encrypted payload can include generating a decryption key based on the password and the salt. Decrypting the encrypted payload can further include decrypting at least a portion of the encrypted payload using the decryption key and the salt.

In another aspect, a method performed by a computing device comprises: encrypting information comprising a secret and a public key of the computing device using a public key of a remote system; sending the encrypted information to the remote system; receiving a response to the encrypted information from the remote system and decrypting the response using a private key of the computing device; determining at a first time that the decrypted response matches the secret and based thereon: verifying that the computing device is connected to a first network; and verifying that the computing device is located within a first geofence.

In one implementation, the method further includes determining at a second time following the first time that the computing device is not connected to the first network or is not within the first geofence and, based thereon, performing an action. The action can be one or more of: erasing application data stored on the computing device, erasing an application stored on the computing device, and sending a message to the remote system.

In another implementation, the method further includes determining that a location of the computing device has changed. Determining at the second time can further include determining that the computing device is connected to a second network wherein the second is not an approved network. The secret can be a random number, and the computing device can be a wearable computing device.

In a further implementation, verifying that the computing device is connected to a first network includes verifying that a service set identifier (SSID) of a network that the computing device is connected to matches an SSID for the first network.

In another aspect, a method performed by a computing device comprises: providing an interface for authoring a procedural workflow; receiving, via the authoring interface, a selection of one or more primitives, wherein a particular primitive comprises an element of interaction between a user and a data item; defining a step of the procedural workflow based on the selected primitives; displaying, via the authoring interface, a plurality of different views, each view comprising a rendering preview of the procedural workflow on a different user device.

In one implementation, the method further includes deploying the procedural workflow to a user device for execution on the user device. The method can further include storing the procedural workflow in an XML-based format. The method can further include providing a scheme that defines a plurality of primitives and how subsets of the primitives can be combined to form steps of a procedural workflow. A particular primitive can include one of an element for capturing, using a device executing the procedural workflow, one of an image, a text input, an option input, a voice input, a video, a bar code, a Quick Response Code, and a beacon signal. A particular user device can include a tablet, a smartphone, smart glasses, or a smart watch.

In another implementation, the method further includes storing the defined step in a step library for reuse in other procedural workflows. The method can further include receiving a definition, via the authoring interface, of an approval flow for the procedural workflow, wherein the approval flow comprises a plurality of approval stages in which the procedural workflow is approved or rejected prior to deployment.

In a further implementation, defining the step of the procedural workflow includes receiving, via the authoring interface, an ordering of the selected primitives, and defining the step based further on the ordering. The method can further include defining a plurality of steps of the procedural workflow based on sets of primitives selected and configured via the authoring interface.

Other aspects of the above include corresponding systems and computer programs. The details of one or more implementations of the subject matter described in the present specification are set forth in the accompanying drawings and the description below. Other features, aspects, and advantages of the subject matter will become apparent from the description, the drawings, and the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the implementations. In the following description, various implementations are described with reference to the following drawings, in which:

FIG. 2 depicts an example method for Quick Response Code authentication.

FIG. 3A depicts an example communication diagram for secure information transfer using Quick Response Codes.

FIGS. 21A-21C depict example analytics screens for data collected during the execution of procedural workflows.

DETAILED DESCRIPTION

Systems and methods are presented for engaging in procedural workflows, multimedia communication, remote assistance, training, data entry, inventory management, authentication, and secure networking using a hands-free or substantially hands-free wearable digital device, such as the Google Glass® or Microsoft HoloLens® headsets. The techniques disclosed herein are applicable to a variety of fields including, but not limited to, healthcare and industrial fields such as energy, oil & gas, manufacturing and maintenance (such as aerospace and automotive), field service, transport and logistics, warehousing, distribution and retail, and construction.

Authentication and Data Transfer Using Quick Response Codes

Figure 1:
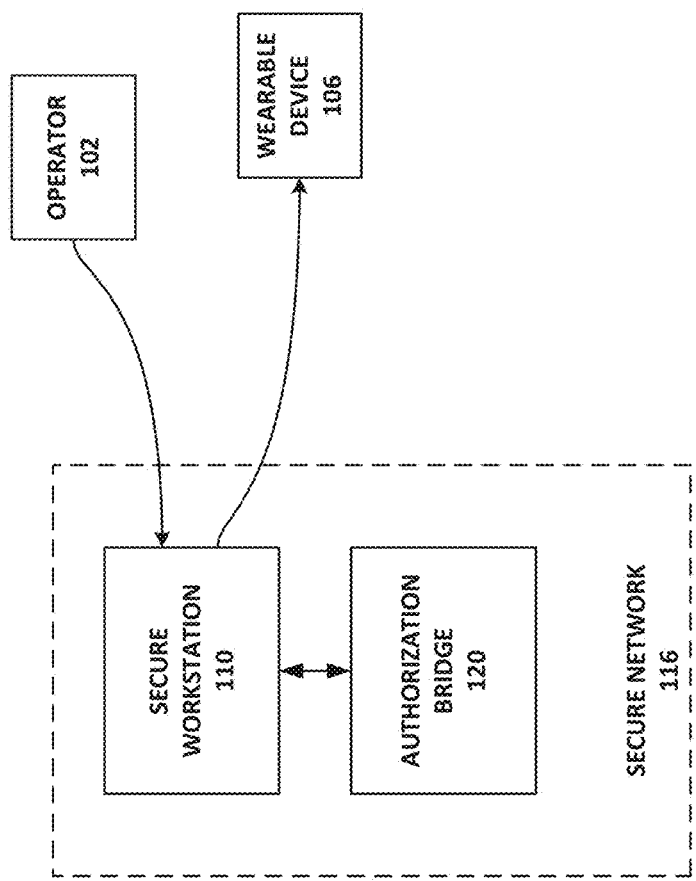
FIG. 1 depicts an example system architecture for Quick Response Code authentication.

In one implementation, referring to FIG. 1, an operator 102 authenticates with a device 106 (e.g., a wearable device, such as Google Glass® smart glasses) using a wearable-optimized, QR-code based single-session user authentication mechanism. The authentication scheme involves the use of a secure workstation 110, handheld mobile device, or other device in combination with the wearable device 106. The session authentication mechanism provides for the use of the wearable device 106 among multiple users in an enterprise setting, in contrast to the typical use of a wearable device (particularly Google Glass® smart glasses), in which the typical wearable device is tied to a single user and session data and other properties are not a concern.

Referring now to FIGS. 1 and 2, in an example authentication process, an operator 102 first logs into a secure workstation 110 or other device within an organization's secure network 116 using his or her existing credentials with the organization. A server-side component can exist within the secure network that acts as an authorization bridge 120 between the organization credentials and temporary session-based credentials that authorize the operate to use the wearable device 106. Once the user is authorized (STEP 202), the organization credentials allow communication with the authorization bridge 120. In STEP 204, the authorization bridge 120 generates a temporary user/session that is linked to the existing organization credentials and defined for a finite amount of time (e.g., session length can be defined in hours, days, until the wearable device 106 is removed, etc.). To link the wearable device 106 with the operator's organization credentials, in STEP 206, the authorization bridge 120 generates a Quick Response (QR) code, bar code, or other scannable code containing a secure token along with encoded session information, such as session length, conditions for the end of the session, and so on. In STEP 208, the QR code is displayed to the operator 102 via a webpage or application that is in communication with the authorization bridge 120. For example, the QR code can be displayed on the secure workstation 110. The QR code can then be scanned by a camera on the wearable device 106, and the session token is extracted and stored and used to identify the operator 102 in question for the duration of the session.

In some instances, the authorization bridge 120 or other server-side component is configured to retrieve additional data from the internal systems of the organization and provide it to the authenticated device 106 (e.g., data specific to the operator, the operator's session, the operator's workspace, the operator's tasks, and so on). The authorization bridge 120 can also retrieve data from external systems (e.g., updates to the device software, etc.) and transmit it to the wearable device 106. In one example, an encrypted payload is transmitted to the wearable device 106 using a QR code (STEP 210). The payload can be transmitted from the secure workstation 110 (or another device) to the wearable device 106.

In further implementations, authentication can be performed by carrying a Bluetooth-low-energy-enabled biometric key-fob. The key-fob can require the operator 102 to authenticate himself or herself by a biometric scan, such as a fingerprint reading, which is compared to a previous reading captured upon the operator's enrollment with the biometric device.

Figure 3B:
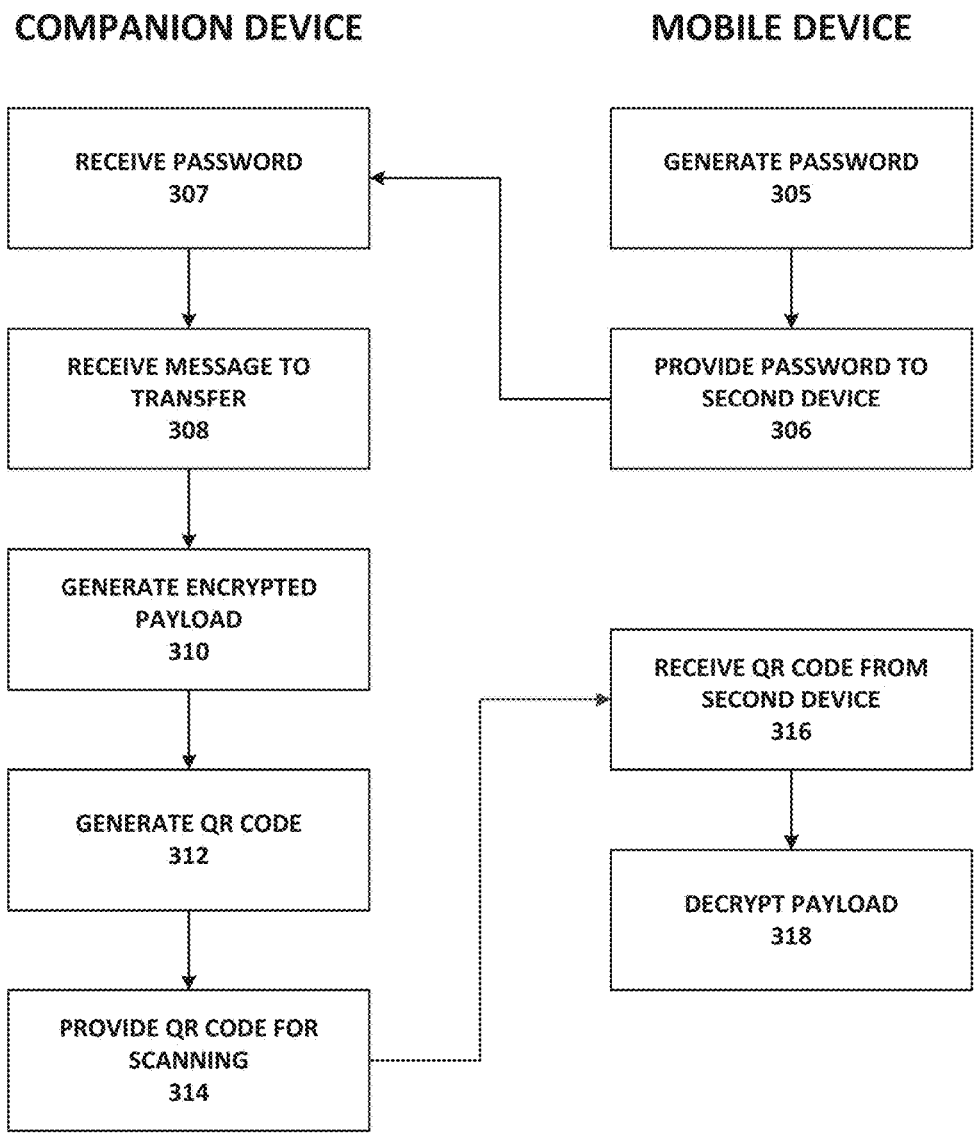
FIG. 3B depicts an example method for secure information transfer using Quick Response Codes.

FIG. 3 depicts one implementation of a platform-independent system that allows sensitive data transfer via QR codes. In this instance, the system includes two devices and a communication protocol between them, although communication among more than two devices is contemplated. One of the devices is a mobile device 302 with limited user input capability, such as smart glasses or a smart watch, and the other device is a companion device 304 with a more flexible user input system such as a real or virtual keyboard. The companion device 304 can be, for example, a mobile phone, a tablet, a workstation, or a terminal displaying a webpage. The protocol that is used for communication between the devices 302, 304 is designed to provide adequate security for transfer of sensitive information such as user credentials, be stateless, and be simple to implement.

In order to transfer non-binary data, a common format can be used between the devices 302, 304. Due to the limited bandwidth of QR codes and the devices that can scan them, it was determined through trial and error that a reasonable QR code length is around 110 bytes for devices such as Google Glass® smart glasses. Because of this limit, the transfer format should be efficient for a variety of input data. Based on these requirements and the ease of implementation, in one example, UTF-8 is a useful format for textual data representation. As the target data to be transferred, such as login credentials, is most likely made up of ASCII characters or other European languages, UTF-8 on average should yield binary streams that are smaller than UTF-16 or UTF-32 encoding formats. Therefore, in this example, before encoding the data in the QR code, the data is converted to UTF-8 first, unless that is otherwise the native encoding of the platform/software.

On modern UNIX-based systems, a library that obtains random data from /dev/urandom is generally sufficient for cryptographic use. Such systems include GNU/Linux derivatives, FreeBSD/OpenBSD/NetBSD, Darwin/OSX, and the like. To enhance security, the libraries in use should not generate entropy in userspace, and should not use /dev/urandom as a seed.

In one implementation, to provide for a better user experience while still maintaining adequate security, the single use encryption password is 14 random characters from the ASCII set [0-9a-z]. In order to extend this key to 256 bits, password-based key derivation function 2 (PBKDF2) is used. Secure Hash Algorithm-256 (SHA-256) can be used as a digest psudo-random function (PRF) function for PBKDF2; however it is possible to use SHA1 if the iteration count is high enough to make PBKDF2 execute in a reasonable amount of time (e.g., at least 80 ms).

Due to asymmetric ciphers, such as RSA with 2048-bit keys, generating relatively large ciphertexts, a symmetric cipher can be used for encryption. In testing, it was noted that a QR code with more than 110-120 bytes was too difficult for Google Glass® smart glasses to scan. Specifically, Advanced Encryption Standard (AES) in cipher feedback (CFB) mode was chosen as a symmetric encryption cipher. Due to the nature of this system, it is not required that the chosen mode of operation provides authentication, as there is limited chance for an attacker to tamper with the QR code. Also, not all Android®-based platforms provide authenticated modes of operation for the symmetric block ciphers.

In one implementation, to provide for easier entry of the 14-character random password string into the companion device user interface, the companion device user interface can allow the 14-character random string to be entered as a set of two 7-character strings. Consequently, the mobile device 302 would present the random string to the user as a set of two 7-character strings. Other methods of providing the password by the companion device 304 to the mobile device 302 are contemplated.

In order to avoid using stale encryption keys, the mobile device 302 can regenerate a password every 60 seconds or some other fixed or variable period. This gives a user up to the time period to enter the required information into the companion device 304 and, in some instances, scan the QR code generated by the companion device.

As this proposed system can be used to handle very sensitive user information, it is imperative that the user is not tricked into entering the user information into an unsecured companion device.

In one implementation, to minimize information leaks, plaintext is padded to the length of a fixed number of bytes (e.g., 64 bytes) using 0x0 (NULL) bytes or some other character. The padding can be performed after the input conversion to UTF-8, and after UTF-8 is represented to the system as a stream of raw bytes. Because NULL bytes are used for padding, other ASCII/UTF-8 control bytes can be used as field separators within the message.

Figure 4:
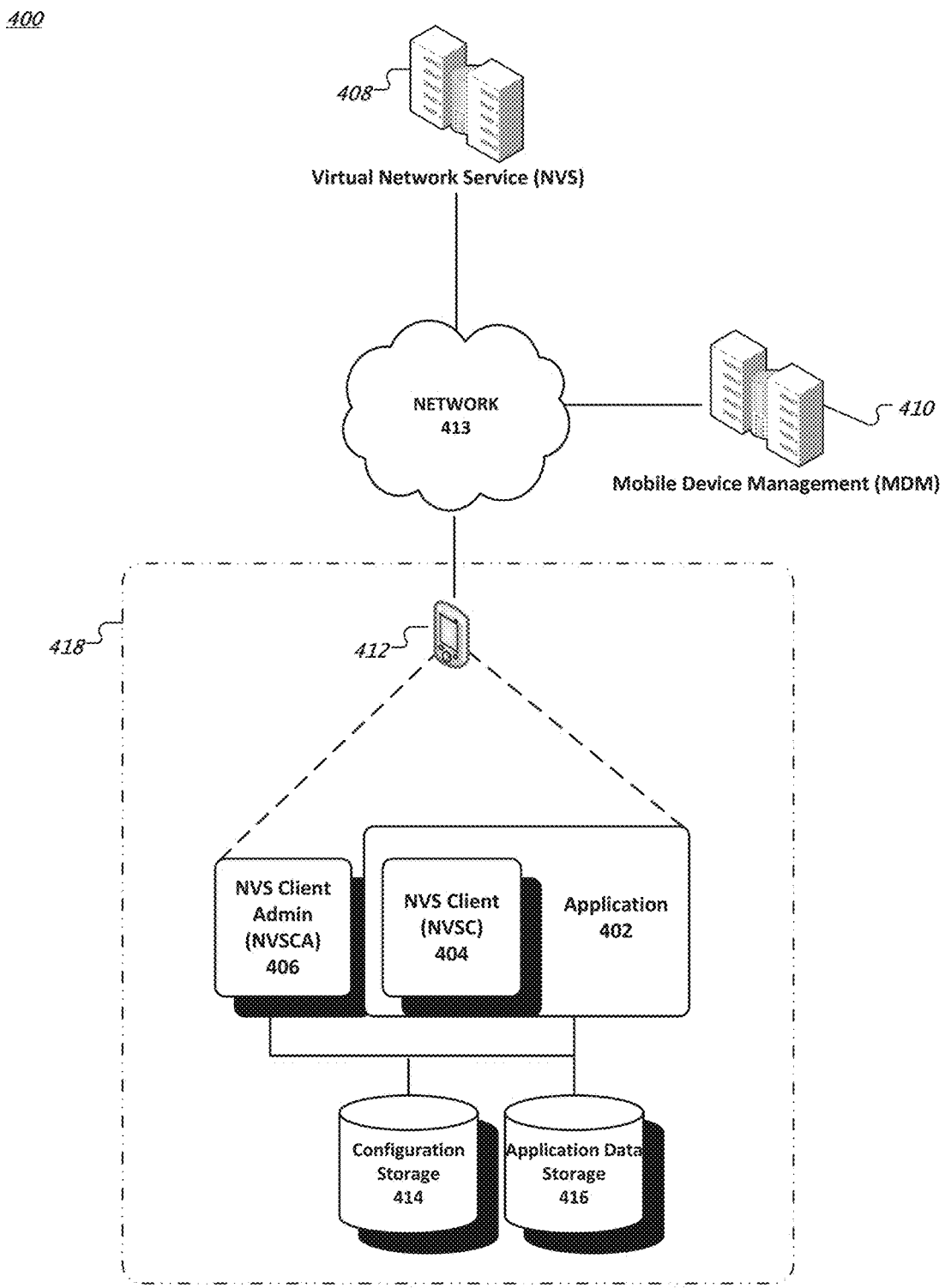
FIG. 4 depicts an example system for securing an application on a client computing device.

FIG. 4 depicts one implementation of a communication protocol for securely transmitting data between a mobile device 302 and a companion device 304. In STEP 305, an encryption password (e.g., 14-character random string generated from the alphanumerical set [0-9a-z]) is generated on the mobile device 302 and is presented to a user. The password can be continuously regenerated (e.g., every 60 seconds) to avoid stale codes being used for encryption. The mobile device 302 then waits for a QR code to be scanned.

In STEPS 306-307, the password is then provided to and received at the companion device 304 (e.g., the same or different user can manually enter the password at the companion device or it can be transmitted in some other manner). Along with the encryption password, a user can enter information (e.g., a message) in the companion device 304 to be transferred to the mobile device (STEP 308). The message can be user credentials, such as a username and password, and/or other sensitive data.

In STEP 310, the companion device 304 generates an encrypted payload. In one implementation, the encrypted payload is generated as follows. Initially, the user input message is converted from the system/application native encoding into UTF-8. The resulting raw bytes are used as plaintext. If the resulting length in the raw binary form is greater than 64 bytes, the input is not accepted and the operation is aborted. It should be noted that, in this example, only the raw bytes are counted and not the characters in the UTF-8 message, as the number of characters in the message can be less than the actual number of bytes used to represent the message in UTF-8.

A salt is generated in the form of a 16-byte random initialization vector (IV) using a cryptographically secure pseudo-random number generator (CSPRNG), and the UTF-8 encoded message is padded to 64-bytes with 0x0 (NULL) bytes to obtain plaintext.

The PBKDF2 key derivative function (KDF) is used to generate a 256-bit key that will be used for the actual encryption. Specifically, the originally supplied encryption password that was converted to UTF-8 is used as the input password to the key derivation function, and the IV is used as the salt. In this example, the number of iterations is set to 5000 and SHA-256 is used as a pseudorandom function PRF. The padded plaintext is then encrypted using the encryption key derived using the KDF and the IV with an AES cipher in the CFB mode of operation, with a segment size of 128 bits and no padding. This generated ciphertext is prepended with the non-encrypted IV to obtain the payload (IV+encrypted payload portion). The payload can then be Base64 encoded.

In STEP 312, the Base64-encoded payload is used to generate a QR code with the pixel size is set to 7 and the error correction level set to L (low). However, other QR code configurations are contemplated. The QR code is then presented by the companion device 304 for scanning by the mobile device 302 (STEP 314). In some instances, the QR code is erased after a certain amount of time (e.g., 30 seconds), and/or manually by the user.

In STEP 316, the QR code is received from the companion device 304 and the payload is decrypted to obtain the transmitted information (STEP 318). In one implementation, the payload is decrypted as follows. First, the QR code is Base64-decoded to obtain the payload. The first 16 bytes from the payload are assigned to the initialization vector (IV), and the remainder of the payload is assigned to be the ciphertext.

The PBKDF2 key derivative function is used to generate a 256-bit key that is used for the actual decryption of the ciphertext. The encryption password originally generated by the mobile device 302 in STEP 402 is converted to UTF-8 encoding and is used as the input password to the KDF, and the assigned IV is used as the salt. Further, in this example, the number of iterations is set to 5000 and SHA-256 is used as the pseudorandom function. Plaintext is then obtained by decrypting the assigned ciphertext using the derived key and assigned IV with an AES cipher in the CFB mode of operation, with a segment size of 128 bits and no padding. The 0x0 (NULL) bytes are then stripped from the resulting plaintext to obtain the original message.

Secure Connectivity

In one implementation, a wearable or other user device is bound to a specific organizational (e.g., corporate, clinical) secure network. The device can automatically lock to a splash screen and/or prevent the use of some or all functionality unless the device is connected to that specific network. In another implementation, the device is bound to a specific geographical premise. The device can automatically lock to a splash screen and/or prevent the use of some or all functionality unless the device is within the defined geographical area. In other circumstances, the device can be partially useable outside the geographical area but restrict access to an internal network and/or sensitive data, such as patient records.

User devices can be bound to a specific organizational network and/or geographical premises using one or more techniques. In one implementation, a device is bound to the foregoing via a connection to one or a series of Wi-Fi networks. As a primary measure, to be bound to the network/premises the device can be securely connected to the organization Wi-Fi network(s) using certificate-based credentials. Without this secure connection, the wearable device is considered unauthorized and can be locked or placed in a state of reduced functionality. As a secondary check, even if the device is connected to the organizational network, the device can still be deactivated if it is determined to be located outside of a set of permitted locations. For example, the wearable device can measure the signal strength of certain Wi-Fi network(s) (whether or not the device is connected) and, if signal strength drops below a threshold strength for a certain period of time, the device can be disabled. Upon returning to a permitted location and/or reconnecting to the organization network, the features of the device can be automatically re-enabled.

In other instances, the operator can reauthenticate (e.g., with a QR code) to continue using the device. Other implementations can use various binding techniques instead of or in addition to Wi-Fi network connection and signal strength analysis. For example, the wearable device can include a GPS module that provides location information for the device. The permitted areas of use for the device can be defined using geofences, such that features of the device can be disabled and/or enabled when a geo-fence is crossed.

FIG. 4 is an example system 400 for securing an application on a client computing device. The system comprises one or more client computing devices (e.g., client computing device 412) such as smart phones or wearable devices. The client device 412 includes one or more software applications (e.g., application 402) that depend on the system 400 for security. The client computing devices can communicate with a network verifier service (NVS) 408 and, optionally, a mobile device management system (MDM) 410 using one or more wireless networks (e.g., network 413). The NVS 408 and the MDM 410 functionality can be implemented on one or more computing devices such as a data center, for example. The NVS 408 is a service that provides an ability for an application to verify that the network 413 that the device 412 is connected to is an approved network. The optional MDM 410 is a system that controls security and authentication policies on the client device 412. Such policies can control which networks the client device 412 is permitted to communicate over, one or more geofences that the client device 412 must be located in (a geofence is a geographic area having virtual boundaries), and what resources a software application 402 executing on the client device 412 can access and the level of access. For instance, storage of the application 402's data 416 can be controlled by policies that define which processes on the client device 412 can access the storage 416. The policies can be stored in the configuration storage 414 on the client device 412.

The client device 412 includes a NVS client administration component (NVSCA) 406 and an NVS client component (NVSC) 404 that resides within the application 402. The application 402 can query the NVSC 404 in order to determine if the client device 412 is located in an approved geofence and is communicating over an approved network. The configuration storage 414 stores configuration data for the NVSC 404 such as MDM policies. The NVSCA 406 is used when the client device 412 is not under control of MDM 410 policies or as an additional component alongside MDM policies. If present, the NVSC 404 can communicate with the NVSCA 406 component to perform actions that otherwise cannot be performed by an application 402 containing the NVSC due to application permissions. In various implementations, communication between the NVS 408, NVSC 404 and the MDM 410 uses transport layer security to provide secure communication. In some implementations, the NVS 408 can also be used by the NVSC 404 to attempt to ascertain if the client device 412's environment is being altered. For example, the client device 412 can use data packet round trip times to determine if the distance between NVS 408 and client device is within a same geofence. If they are not within the same geofence, it may be likely that the client device 412 is communicating with a fake NVS.

Figure 5:
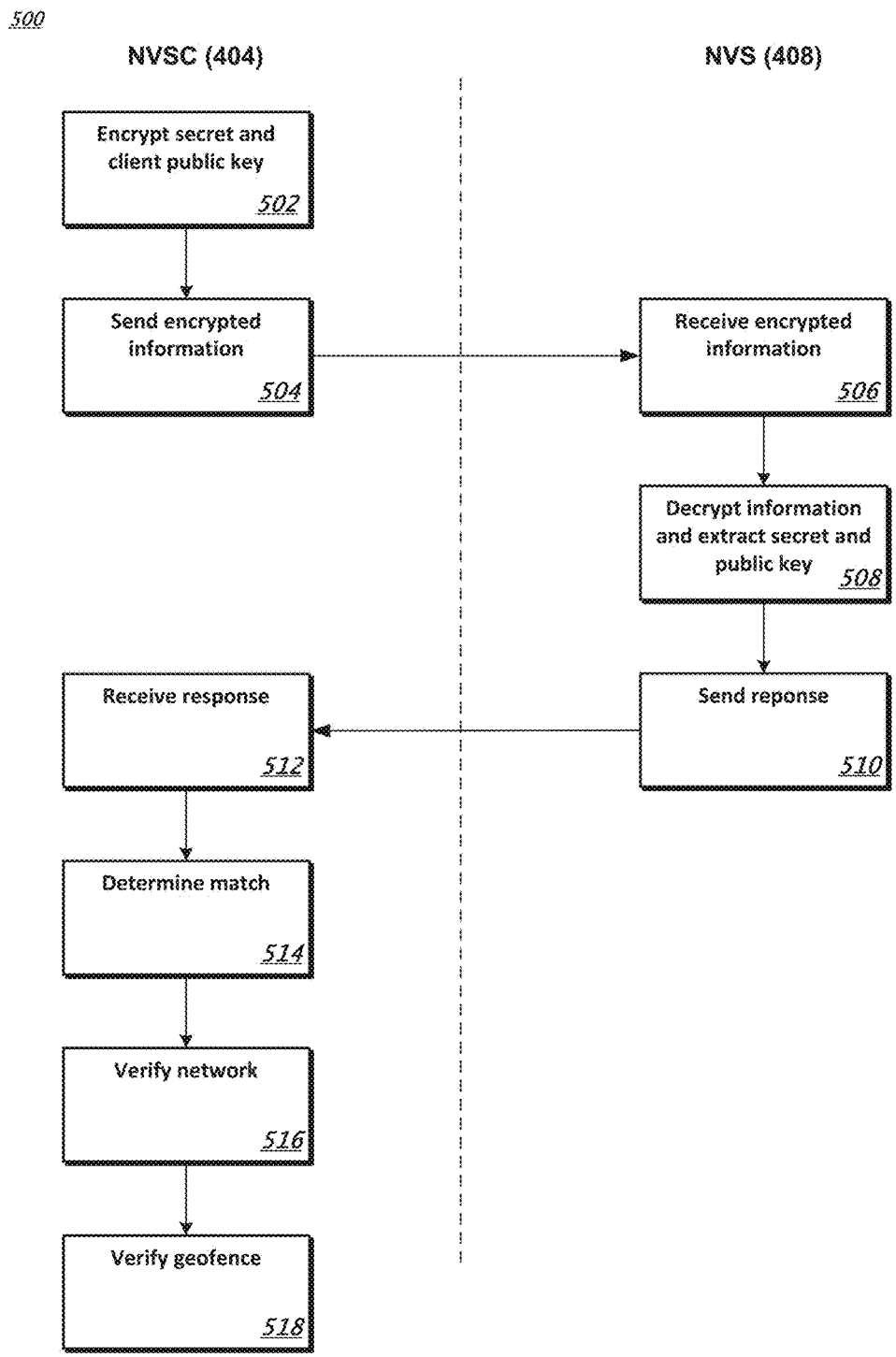
FIG. 5 depicts an example method for initializing a client computing device.

FIG. 5 is an diagram of an example client computing device 412 initialization 500 process. The initialization process 500 can be performed when the application 402 initializes and at various times thereafter to maintain security such as when it is detected that the client device is connected to a new wireless network or has changed physical locations. The NVSC 404 encrypts information comprising a secret (e.g., a random number) using a public key of the NVS 408, and the NVSC appends its own public key to the result (STEP 502). The NVSC 404 sends the encrypted information to the NVS 408 (STEP 504). The NVS 408 receives the encrypted information (STEP 506) and decrypts the information using the private key of the NVS 408 (STEP 508). The NVS 408 extracts the secret from the decrypted information and retrieves the public key that was appended to the encrypted information (STEP 508) and then encrypts the secret using the retrieved public key. The NVS 408 then sends the encrypted secret to the NVSC 404 in response (STEP 510). The NVSC 404 receives the response and decrypts the secret using the private key of the NVSC 404 (STEP 512). The NVSC 404 then determines if the decrypted secret matches the original secret (STEP 514). If not, the initialization process fails. Otherwise, the NVSC 404 verifies that the computing device 412 is connected to an approved network (STEP 516) and is located in an approved geofence (STEP 518). For example, a policy stored in configuration storage 414 can specify the service set identifier (SSID) of a network that the client device 412 is permitted to connect to. Likewise, a policy stored in configuration storage 414 can specify the geographic bounds of a geofence that the client device 412 is permitted to be located in.

If the initialization 500 fails because the received secret key does not match the sent secret or because the client device 412 is not connected to a permitted network or located in a permitted geofence, the NVSC 404 can perform one or more actions such as erasing the application data storage 416, erasing the application 402, erasing the entire storage of the client device 412, sending an alert message to the NVS 408, and attempting to restart the initialization process 500. If the NVSC 404 lacks permission to perform one or more of the aforementioned actions, the NVSC 404 can request permission for doing so from the NVSCA 406. In some implementations, the NVSCA 406 can send a message to the MDM 410 requesting that the MDM 410 direct a MDM proxy process on the client device 412 to perform the action.

Network Integration

In some implementations, a wearable device can act as a bridge to interface with legacy or other systems in an organization's network. For example, in a retail system, as an operator scans product barcodes using the wearable device, various information about the products can retrieved from the organization's legacy inventory system, translated or transformed as necessary, and displayed to operator via the device. Likewise, the operator can scan a number of the same item, gesture that the count is complete, and the wearable device can transmit the inventory count to the legacy system. Data translation, interfacing, and bridge-based computation can be performed on the wearable device, as necessary.

Offline Behavior

In one implementation, the present system is ruggedized for poor or low connectivity states. Data is fetched and cached when the network is available. When offline, the system continues with last-known data and bi-directional transmission payloads are built and queued up for later transmission (when the network is made available again).

Further, the system supports deferred speech-to-text recognition. When no network connection is available, the system first tries to transcribe the spoken audio snippet locally on the device. The device can attempt to recognize spoken keywords that are in the device's local dictionary (e.g., navigational commands, document names, etc.). If this is not possible due to the complexity of the audio captured (e.g., if no keywords are recognized), the system can record and save the audio for later analysis. Once the network connection is restored, the saved audio can be transmitted to a remote server for transcription. If the saved audio included instructions for the device, the system can then attempt to execute the instructions on the device or ask the user for permission to do so.

Figure 6A:
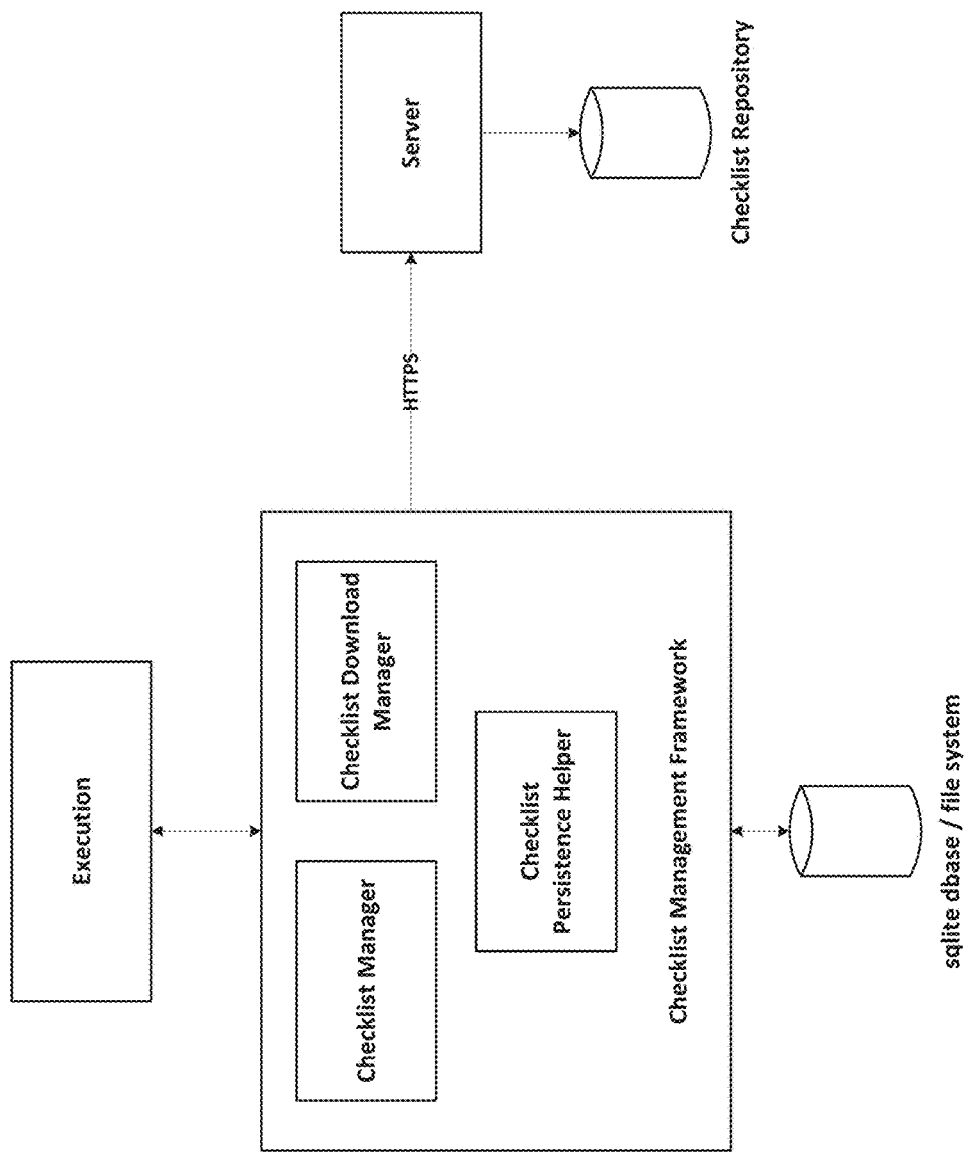
FIGS. 6A and 6B depict example systems for ruggedized checklist execution.
Figure 6B:
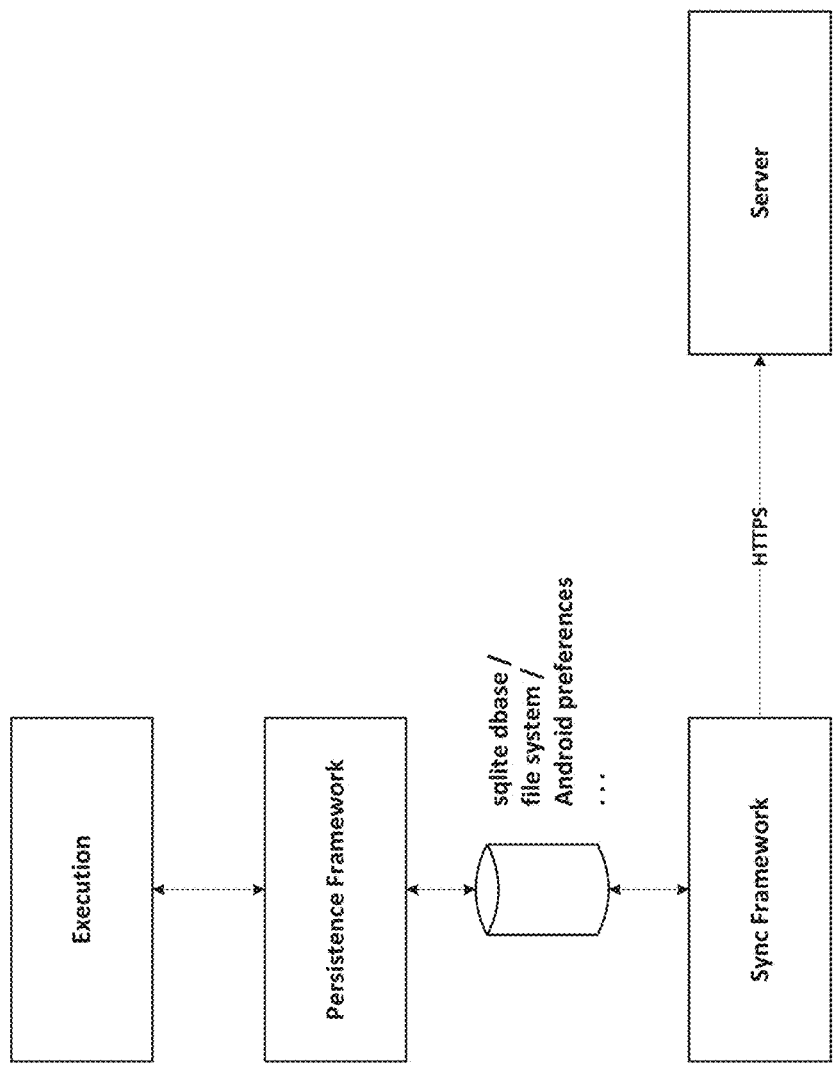

FIGS. 6A and 6B depict an example system architecture that provides a framework for allowing a worker to complete work without network dependency and push data to a server when it becomes available.

A checklist represents the work that the worker can perform. The checklists are hosted in a checklist repository on a server and are synched to a user device when the user logs in or performs a force refresh. The checklists can be downloaded from the server in a compressed format as a single file and can be stored locally on the device in uncompressed state. This allows the user of the system to perform work even when there is no network available. Data generated by the user is stored locally on device storage and is pushed to the server as and when network connectivity is available.

The Checklist Management Framework is responsible for downloading checklists from the server, version management, and storage management. The Persistence Framework provides an application programming interface (API) to store and retrieve data asynchronously to/from different data stores such as SQLite, dBase, flat files, Android preferences, etc. The data stored is persistent and is not lost if the system crashes, restarted, or is updated. The API allows users to store structured data such as date, number, text as well as unstructured data like an image, video, etc.

The Sync Framework is responsible for sending data to the server. It tries to send data to the server when the network is available and batches data to provide optimal network usage. Once the data is sent to the server and an acknowledgement is received, the space is reclaimed for future use. Data is sent to the server in order of when the data is stored, so the server can play back the worker's actions as they occurred on the worker's device. The Sync Framework monitors network connectivity and as soon as the network is available it sends data that is not yet synchronized with the server.

In one implementation, a worker must be connected to a network when logging on to his wearable device for the first time. This allows for the storage of an authentication token from the server, and the downloading of standard work locally to the device. If a network failure occurs while attempting to download a procedural checklist, it can be re-downloaded when opened. This authentication token can last for a certain time period (e.g., 24 hours), after which point the worker will be asked to login again (if on the network). The token can continue to exist even if the worker device is completely restarted or the worker quits a workflow application. The token can be deleted if the worker manually selects a log out option or if the workflow application is uninstalled or the application data is otherwise deleted.

The token can be continually extended (e.g., every hour) as long as the worker has network connectivity and is using the workflow application, so that he or she will not be prompted to login again while active on the network. The worker can also go out into the field in a region not having network connectivity and will be able to use the workflow application completely offline. This includes executing all standard work, and all execution data can be captured and stored locally. In some implementations, even after the expiry of the token, the worker can continue to use the workflow application on the worker's device to execute checklists and capture data locally. When the worker reconnects to the network and the workflow application attempts to upload execution data, if the token has already expired (e.g., it has been more than 24 hours since login/last activity), the worker will be prompted to login before the execution data can be uploaded to the server.

The present system allows multiple workers to perform work offline on the same device, and the data and session information for each worker is stored in separate data blocks and synched to the server when the network is available, Workers are also able to pause and resume a session. Session state can be preserved even if the device reboots or loses power.

Director—Procedural Checklists

Figure 7:
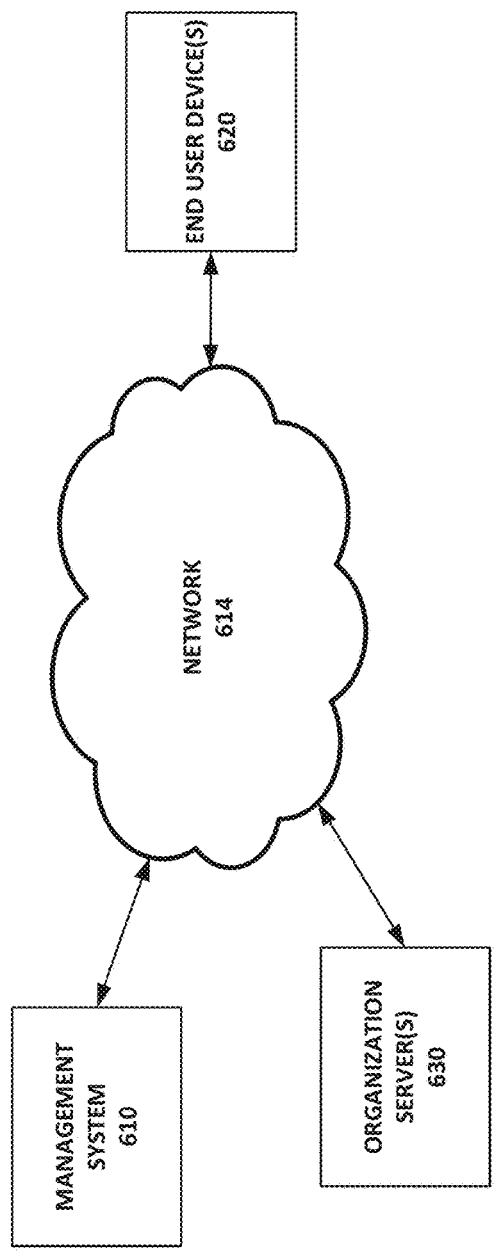
FIG. 7 depicts an example system architecture for procedural workflow authoring and execution.

Referring now to FIG. 7, in one implementation, the workflow and communication system described herein includes a management system 610 that allows a user to create procedural workflows that are deployable to one or more end user devices 620 over a network 614. The workflows are "write once run anywhere," in that a created workflow can be created once and deployed to various different end user devices without requiring customizations per device to properly function. End user devices 620 can be mobile devices such as digital wearable devices (e.g., Google Glasses® smart glasses), smartphones, laptops, tablets, and the like. As noted herein, the end user devices 620 can include software applications that execute procedural workflows created by using the management system 610, that allow for a user to communicate with or be guided/trained by remotely-located personnel, and so on. For example, a software application can execute on an end user wearable headset that enables the user to step through checklists in order to accurately and safely complete company workflows. In addition, users can capture audio, images, video, and other data relating to procedures which can be stored on the management system 610 and can be used for compliance, audit, troubleshooting, and so on.

In an industrial setting, an application for executing procedural workflows (referred to herein as the "Director" application) provides field service operators with a hands-free digital workflow system for performing standardized procedures in conjunction with end user devices 620 that execute the application. The Director application can be navigated with voice commands and head gestures, and in-field data can be captured in the form of dictated messages or point-of-view perspective photos and recorded videos. The Director application can record extensive metrics for workforce analytics such as the length of time taken for the operator to complete each step, which can be used for audit, compliance, and continuous improvement. The data can also be automatically fetched, edited, and uploaded from/to the relevant organization servers 630 (e.g., industrial database systems including but not limited to an inventory management system or a materials management system).

In a clinical setting, the Director application provides healthcare providers with a hands-free digital workflow system for performing standardized exams, tests, or procedures. The Director application can be navigated with voice commands, head gestures, and touch actions, and in-field data can be captured in the form of dictated messages or point-of-view perspective photos and recorded videos. The Director application can record extensive metrics for analytics which can be used for audit, compliance, and continuous improvement. The data can also be automatically fetched, edited, and uploaded from/to the relevant organization servers 630 (e.g., clinical systems, including but not limited to electronic health record (EHR) servers, emergency department trackboards (ED Trackboard), etc.).

In some implementations, the Director application can be executed entirely or partially offline. For example, when the application has network connectivity it can retrieve all or a subset of the standardized procedures to which the operator/user has access. The operator can navigate through a particular workflow in an online or offline state, and the collected result data and analytics can be packaged up locally on the wearable device 620. Upon restoration of network connectivity, the collected data and analytics can be uploaded to a remote organization server 630 for storage and analysis.

Management System

The management system 610 can be instantiated in a secure cloud environment, installed within a company's network, or in a third-party cloud hosted service. This system 610 provides a web-based management interface with a visual authoring interface to create, edit, audit, approve, and delete checklist/workflow procedures to be deployed on operator devices. The management system 610 also provides the ability to also import workflows from XML, Microsoft® SharePoint® documents, and other systems as needed. In addition, the management system 610 can store an audit trail of completed steps and procedures (including time, location, operator ID, steps completed and responses given, video/audio/photo recordings, if applicable, etc.).

In one implementation, the management system 610 has eight main components: (1) a Domain Specific Language (DSL) to specify information transfer between application components; (2) a standard work creation interface having a WYSIWYG editor to create and view procedures backed by the DSL; (3) standard work approval, deployment, and versioning using an approval dashboard; (4) intelligent work scheduling primitives and a standard work scheduling algorithm to assign available work to workers; (5) standard work execution using client devices to capture field data; (6) reporting and displaying data generated by standard work execution; (7) standard work feedback alerts provided to an author using in-application feedback submission; and (8) an administrator dashboard to allow administrative users to define the information structure of a standard work library.

These system components provide for a system where an author can generate a procedure on an authoring dashboard once, and execute/capture data for that procedure on any supported device or context (e.g., a web-based execution on a desktop in a browser, tablet based execution on a tablet device, wearable based execution on Google Glass®, etc.)

Figure 8:
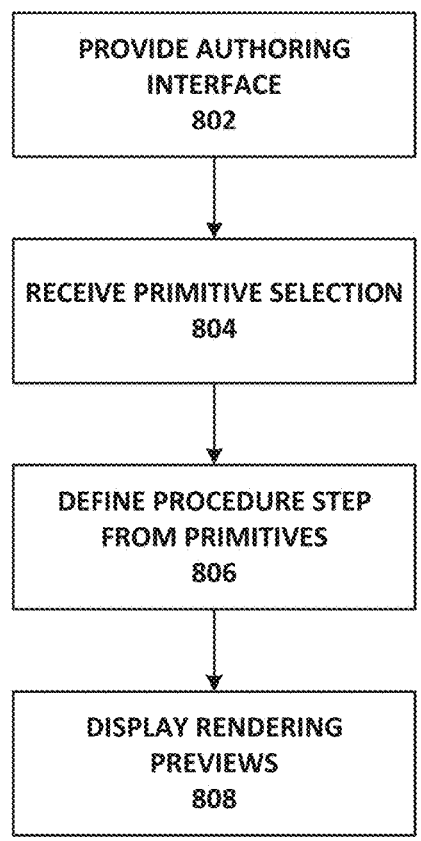
FIG. 8 depicts an example method for procedural workflow authoring.

Accordingly, in one implementation, a method for authoring a procedural flow is depicted in FIG. 8. In STEP 802, the management system 610 provides an interface for authoring the procedural workflow. A user can select, order, and configure one or more primitives (STEP 804) using the interface. Generally, a "primitive" is a component of a procedural step. For example, a primitive can be an element of interaction between a user and a data item, such as image or video capture or display, text entry or display, option selection, and so on. In STEP 806, a step of the procedural workflow is defined based on the selected primitives. Further, in STEP 808, the interface displays one or more rendering previews of the procedural workflow as it would appear on different user devices. In some implementations, workflows are "write once run anywhere," in that customized workflows do not need to be created per unique user device. For example, the same workflow can run on a wearable device and a tablet and, while it may be displayed differently or accept user output, the workflow will proceed through its steps in an equivalent functional manner on each device. The above steps are explained in further detail below.

Checklist Primitives

Procedural checklists can be custom-built from a set of primitives, which cover a wide variety of situations. Additional primitive types can be added to the set. Primitives can include, for example, scanning, getting data, taking transcription, and other basic functions. The management system 610 can include authoring capability to allow for the creation of workflows from combinations of primitives. In one implementation, an XML schema defines the primitives and the manners in which they can be combined to form procedural checklists. Accordingly, a completed workflow can be represented in an XML-based language, such as that described in Appendix A—Wearable Intelligence Markup Language (WIML) (XML), below. In other implementations, WIML can be represented using JavaScript Object Notation (JSON), as shown in Appendix B, below.

The WIML procedures can be processed and composed into instructions compatible with the end-user wearable device 620. The device 620 can execute the instructions to, for example, provide a procedural checklist to the operator, such as those described below. The result of the executed instructions (e.g., the operator's progress through the checklist) can transmitted to a remote server (e.g., organization server 630) along with analytics data relating to the performance of the operator.

As noted above, a DSL can be used to transfer information and encode standard work. The DSL can be encoded in XML documents (referred to herein as WIML documents). In one implementation, each WIML document has 4 elements at the root: a metadata element, a head element, a body element, and a foot element. The metadata element is encoded with metadata related to the standard work, for instance, the name of the author of the document can be listed within the metadata. The metadata also includes the document type. Different document types can be populated with different steps.

The head, body, and foot elements are each populated by "step" elements. A step element represents a single execution frame in a procedure, and steps are composed of customizable primitives that allow users to create their own step architecture. Examples of primitives include a text element that allows the display of text, a picture element that allows the display of pictures, an image capture element that allows the user to capture a picture using the end user device 620, a text input which allows the user to record textual data, and an option input that allows the user to select and record one choice from a list. Other primitives are contemplated. It should be noted that steps are composable and constructed from the primitives.

The primitives that represent data capture during execution allow the captured data to be viewed on an analytics dashboard, described below. The DSL provides for a common data architecture among multiple execution contexts; i.e., a "write once run anywhere" paradigm. Additionally, this construction allows for different input formats on different devices. For instance, a textual input primitive may accept a voice input on a wearable device and a typed input on a tablet.

Figure 9A:
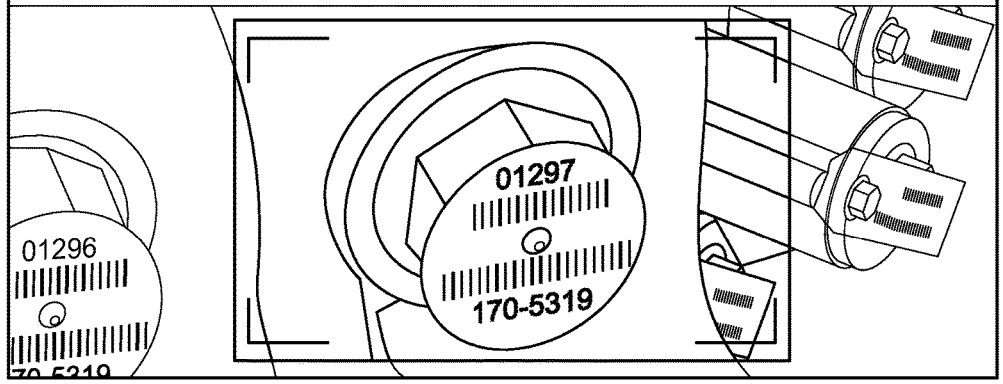
FIGS. 9A-9C depicts example interface screens for authored procedural workflows.
Figure 9B:
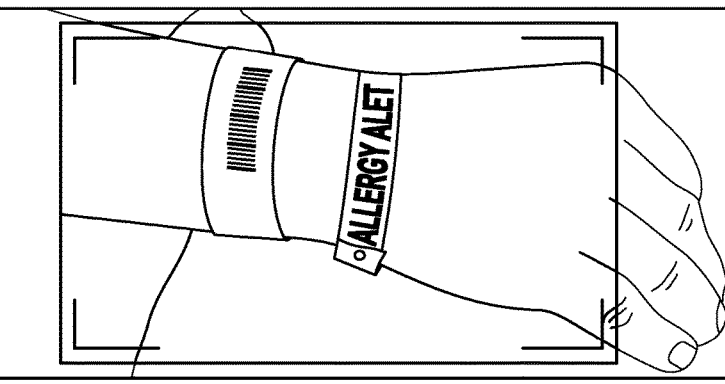
Figure 9C:
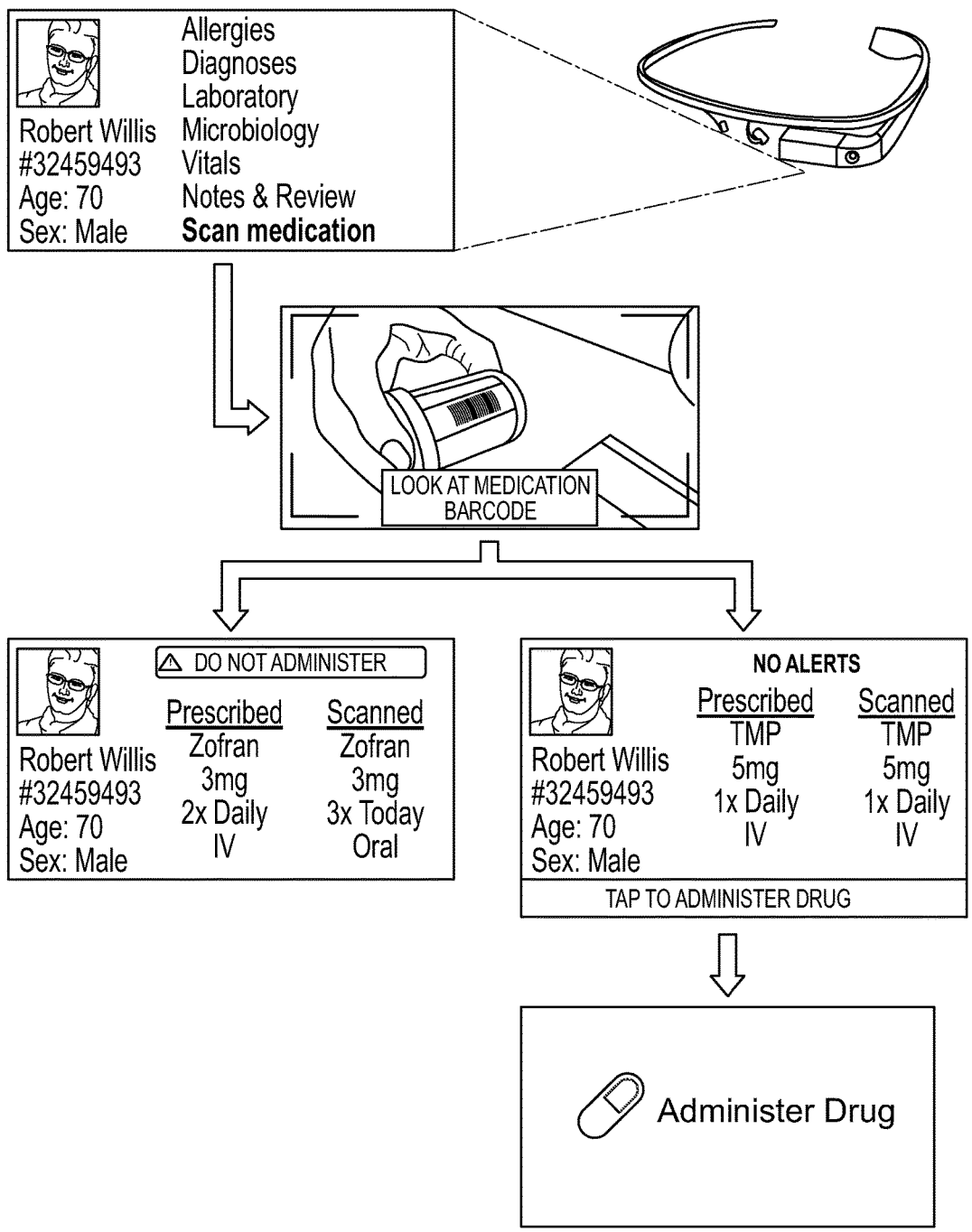

One possible primitive is the capture, scanning, or recognition of a bar code, QR code, text, beacon signal, RFID tag signal, or other object. In one implementation, the wearable device 620 can be used to scan the particular barcode or QR code. In an industrial setting, for example, this feature can be used to identify the tool being worked on or materials that are required to complete a task (see FIG. 9A). In a clinical setting, this can also be used to identify the patient or medications or tools that are required to complete the procedure (see FIGS. 9B and 9C). In either setting, the QR code system can also be used to authenticate a user.

More complex data capture can occur using an end user device 620. For example, the device 620 can include optical character recognition (OCR) and/or object recognition to provide for task commencement and/or other functions through interpretation of text, rather than a barcode or QR code. Image analysis techniques can also be used to recognize objects. For example, a database of industrial objects in three-dimensional form can be maintained, and edge matching, feature matching, and/or other techniques can be used to determine which object or objects are shown in the view of the operator. Based on the object detected, a workflow can be started, a task can be accomplished, and so on. In other instances, Bluetooth beacons and/or RFID tags associated with objects and/or locations can be scanned using the wearable device to start or finish an event.

The "Information Display" primitive does not require a response from the operator, but rather is used to display information to the operator prior to completing a step. For example it can display a "how to" procedure using video, photos, audio and/or text prior to the procedure being performed. Information from the industrial knowledge management systems or the clinical systems can be incorporated, as well as past incidents from the event database to ensure mistakes are not repeated.

Figure 10A:
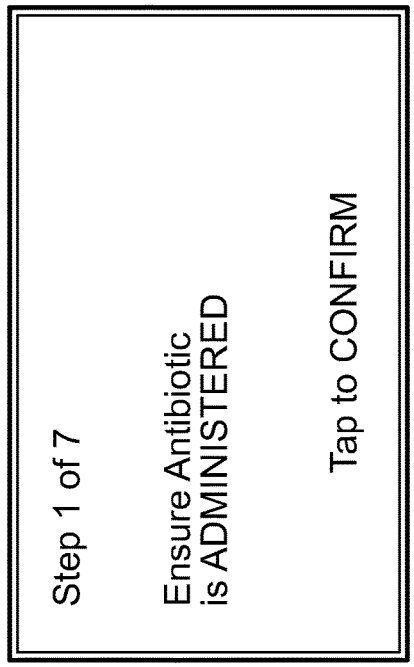
FIGS. 10A-16 depict example primitives and steps in procedural workflows.
Figure 10B:
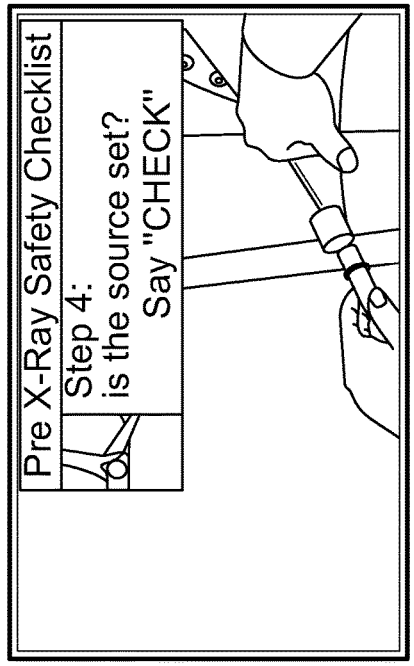

The "Gating Step" primitive supports a step that is gating and must be completed or acknowledged in order to continue to the next step in the checklist. FIG. 10A depicts a text-based gating step primitive that requires user interaction to confirm. FIG. 10B depicts a point-of-view perspective of an operator navigating hands-free (via voice) through a gating step.

Figure 11:
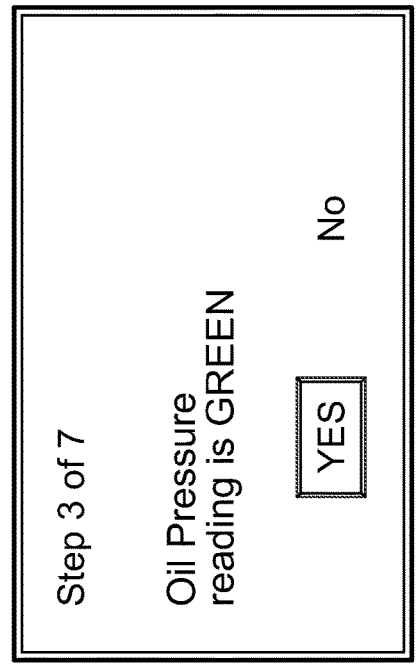

The "Binary Response" primitive supports a checklist step that has a response with one of two values (e.g., "yes/no", "true/false", "successful/unsuccessful", etc.). FIG. 11 depicts an example binary response step as displayed to a user.

Figure 12:
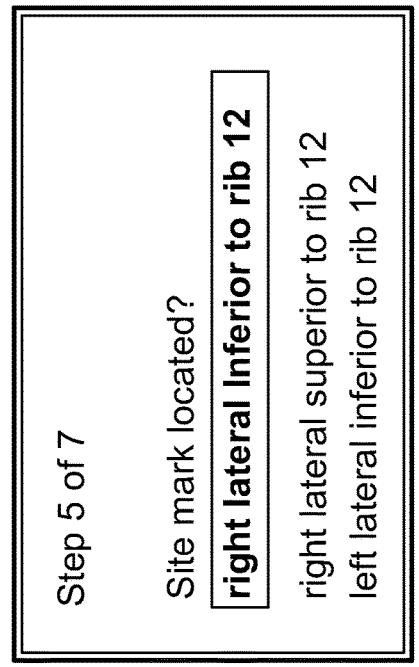

The "Multiple Choice" primitive supports selecting one of an arbitrary number of possible responses. FIG. 12 depicts an example multiple choice step as displayed to a user.

Figure 13:
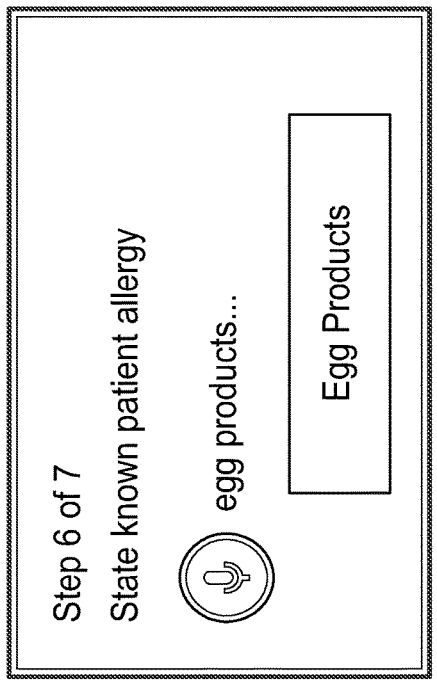

The "Dictated Data Entry" primitive supports a free-form response which is dictated by the operator and transcribed. This primitive can optionally be constrained to, for example, accept only a numerical response. FIG. 13 depicts an example dictated data entry step as displayed to a user.

Figure 14:
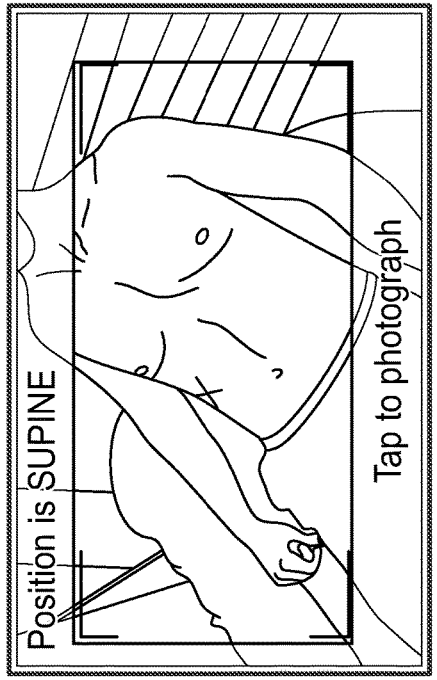
Figure 15:
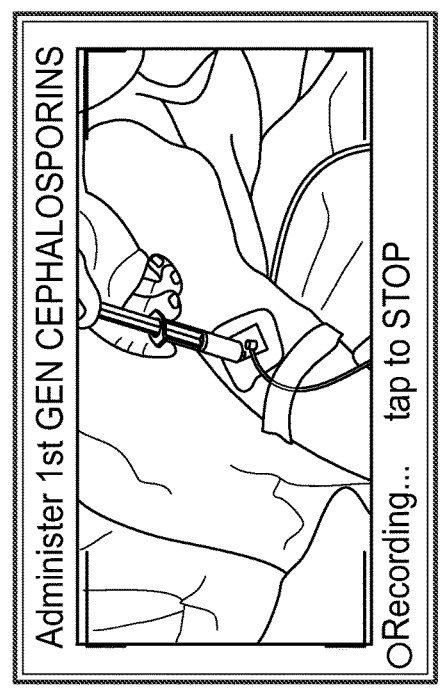

Another primitive supports taking a picture, for example, as a form of compliance that the step is completed (see FIG. 14). Similarly, one primitive supports the recording of a video while the operator is completing a task, for example, as confirmation that the task was done correctly (see FIG. 15).

Figure 16:
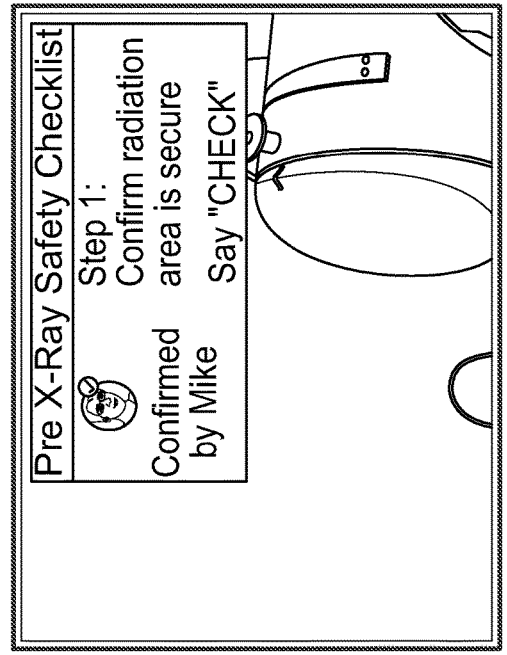

FIG. 16 illustrates an example of the "Multi-party Assent" primitive, which is useful in a multi-person environment, and requires all (or a specified number of) people to agree before the workflow can continue to the next step.

Standard Work Creation Using WYSIWYG Editor

Figure 17A:
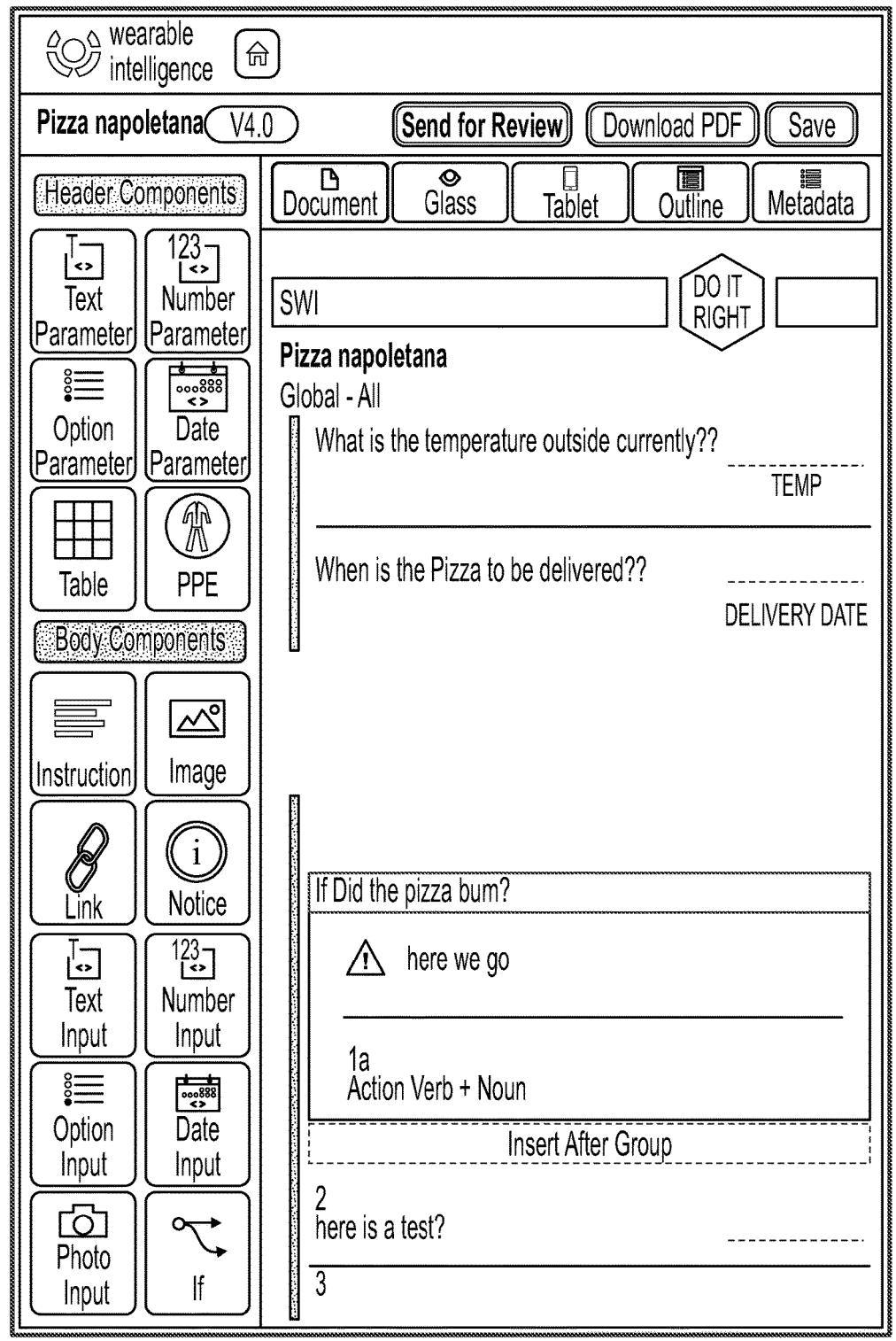
FIGS. 17A-19C depict example user interface screens for a procedural workflow authoring system.
Figure 17B:
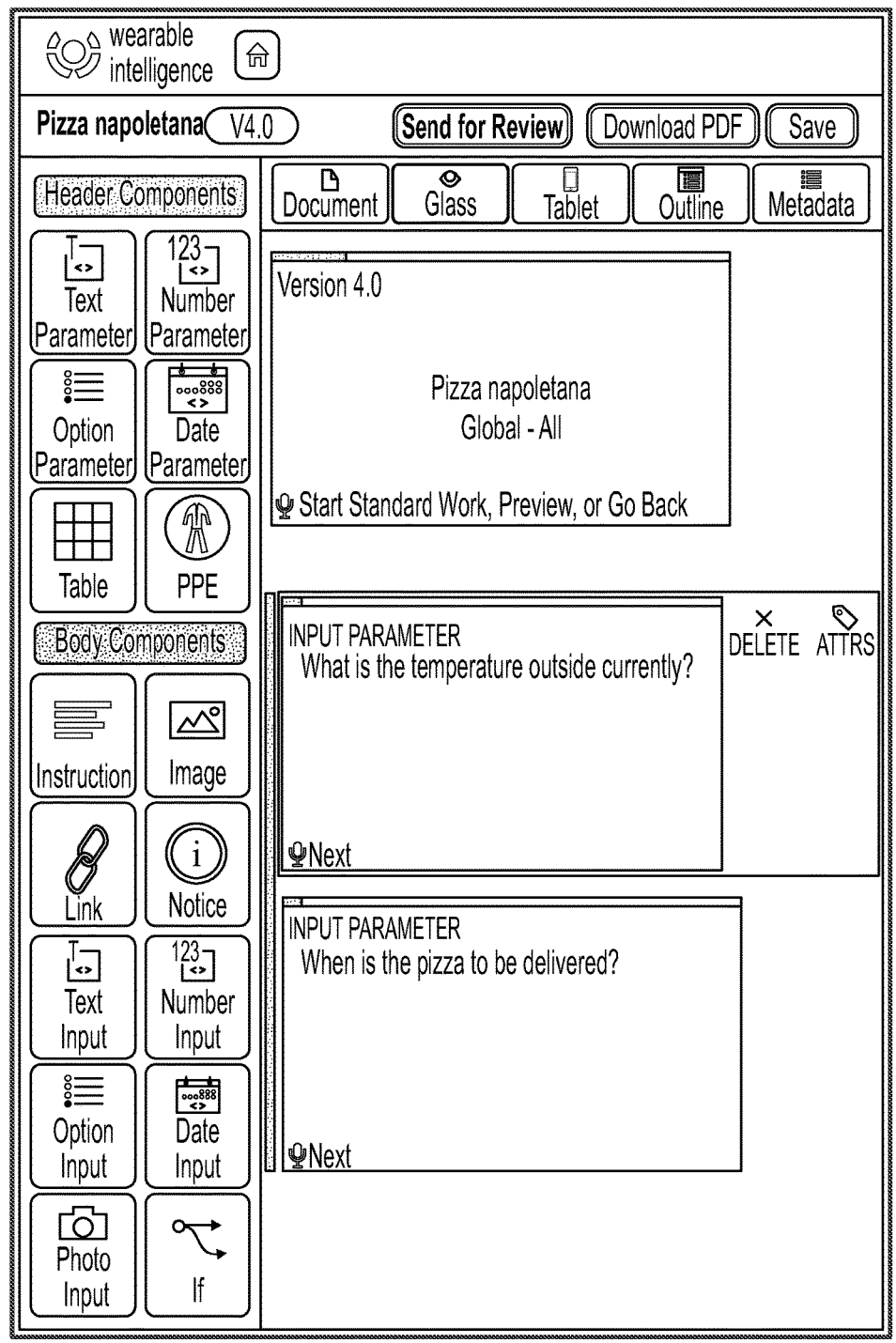
Figure 17C:
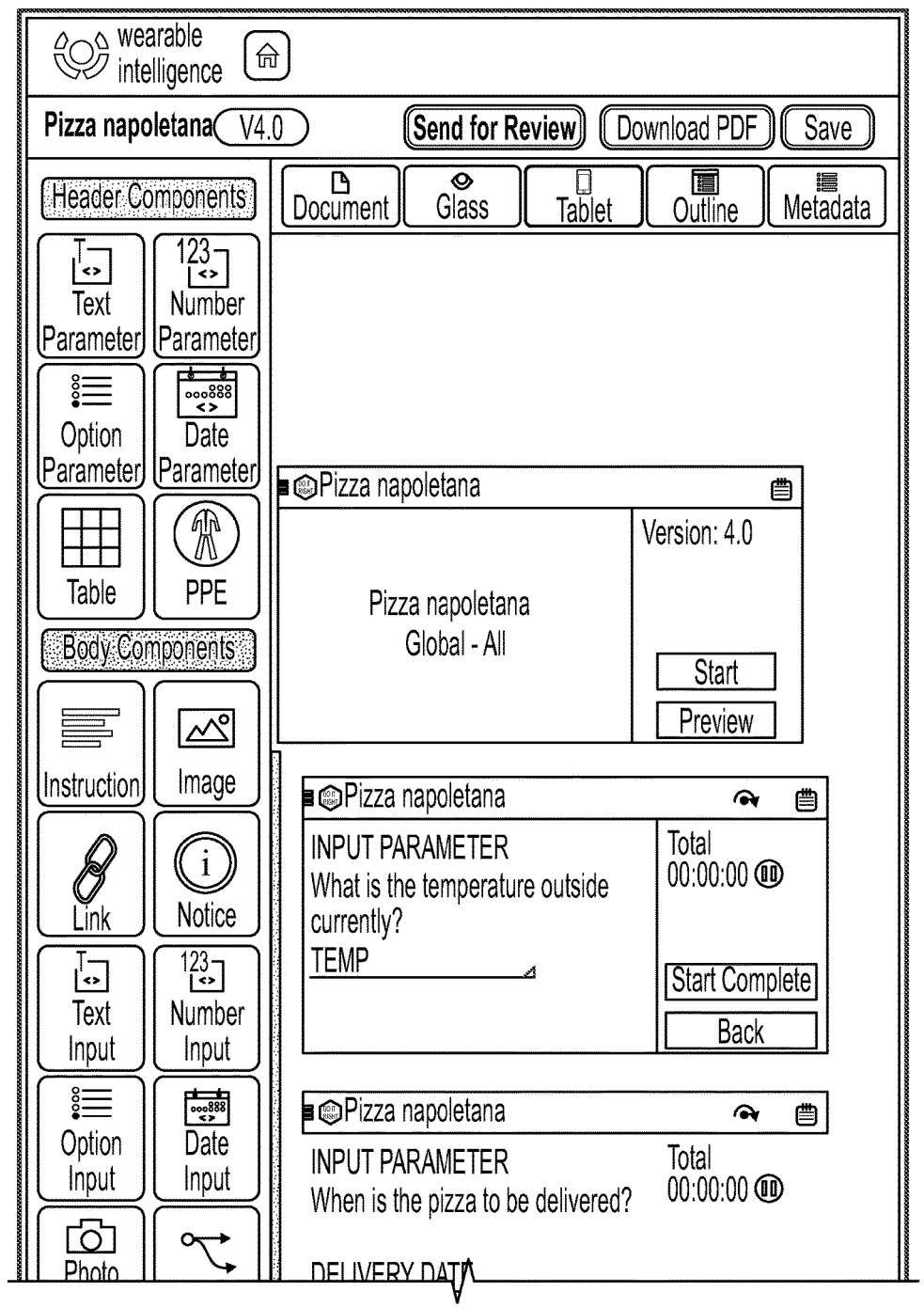
Figure 17D:
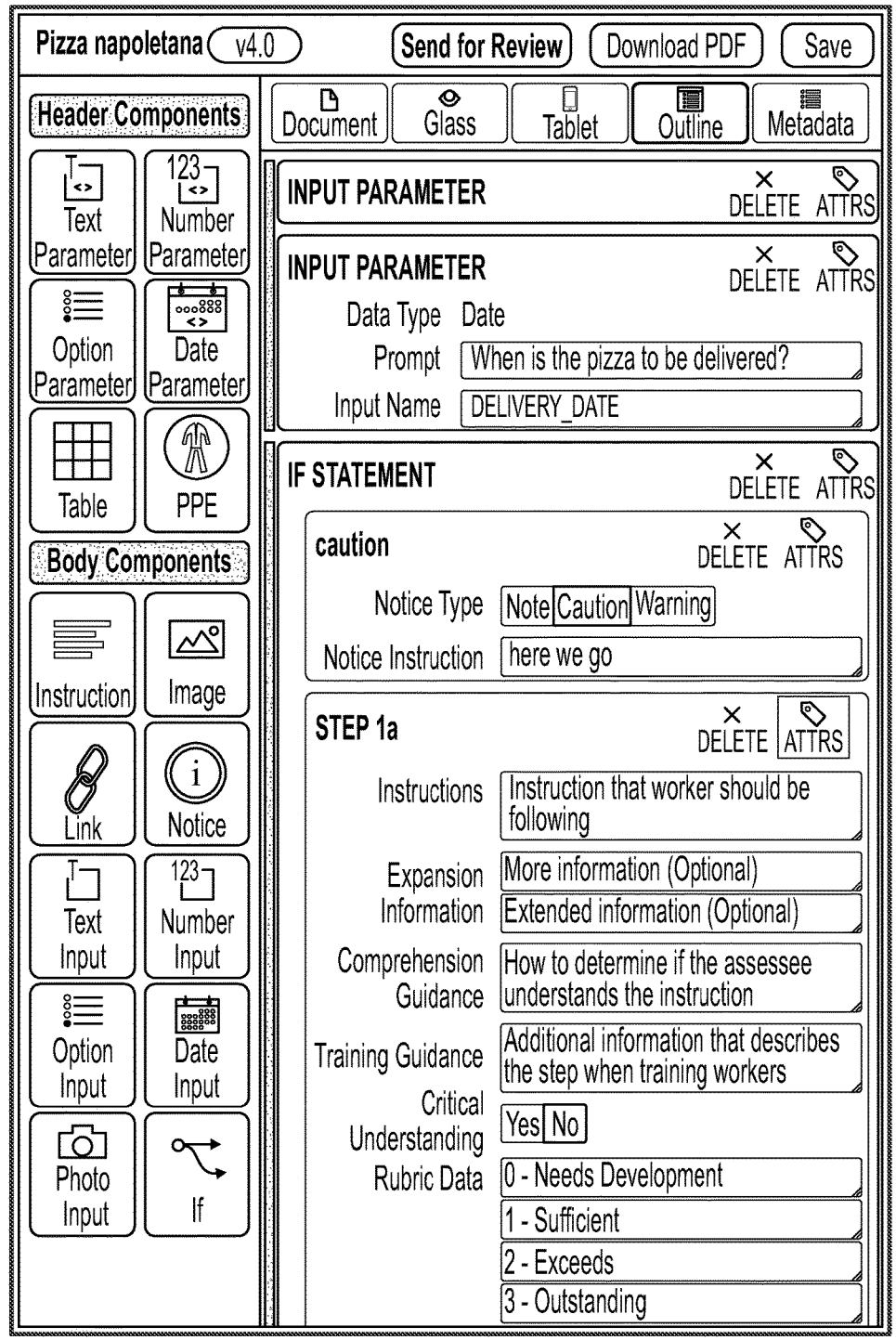

In one implementation, the management system 610 provides an authoring interface that allows users to create and edit procedural workflows in a WYSIWYG editor. The interface allows users to create procedures and edit these procedures in views that simulate how the procedure would be rendered in multiple formats and on multiple devices (e.g., a printed PDF, a tablet, a wearable device, and an unstyled "construction" view). FIG. 17A depicts an example document view for a pizza delivery procedural workflow. FIG. 17B depicts a wearable device view for the same workflow; FIG. 17C, an example tablet view; and FIG. 17D, an example outline/construction view.

Figure 18B:
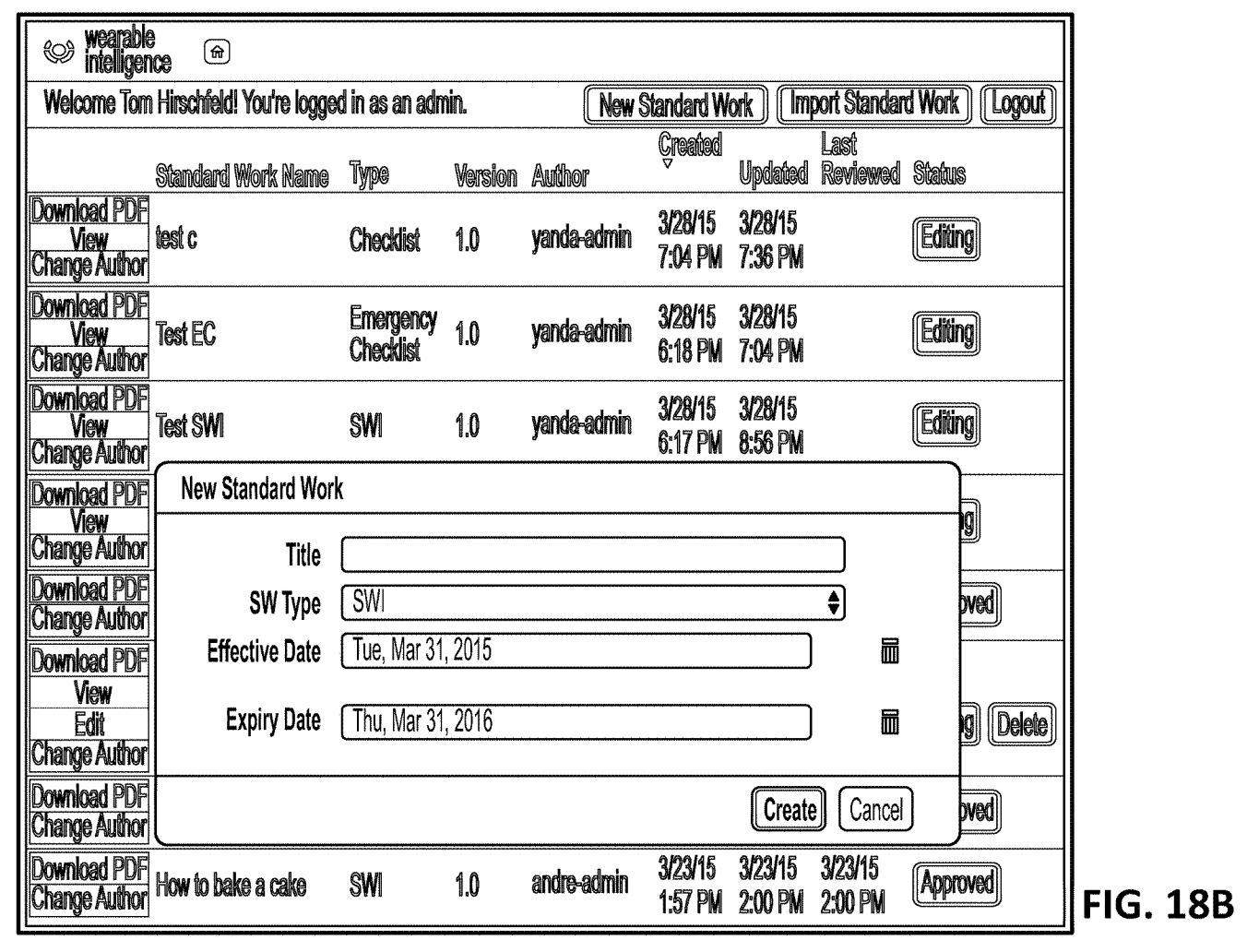
Figure 18C:
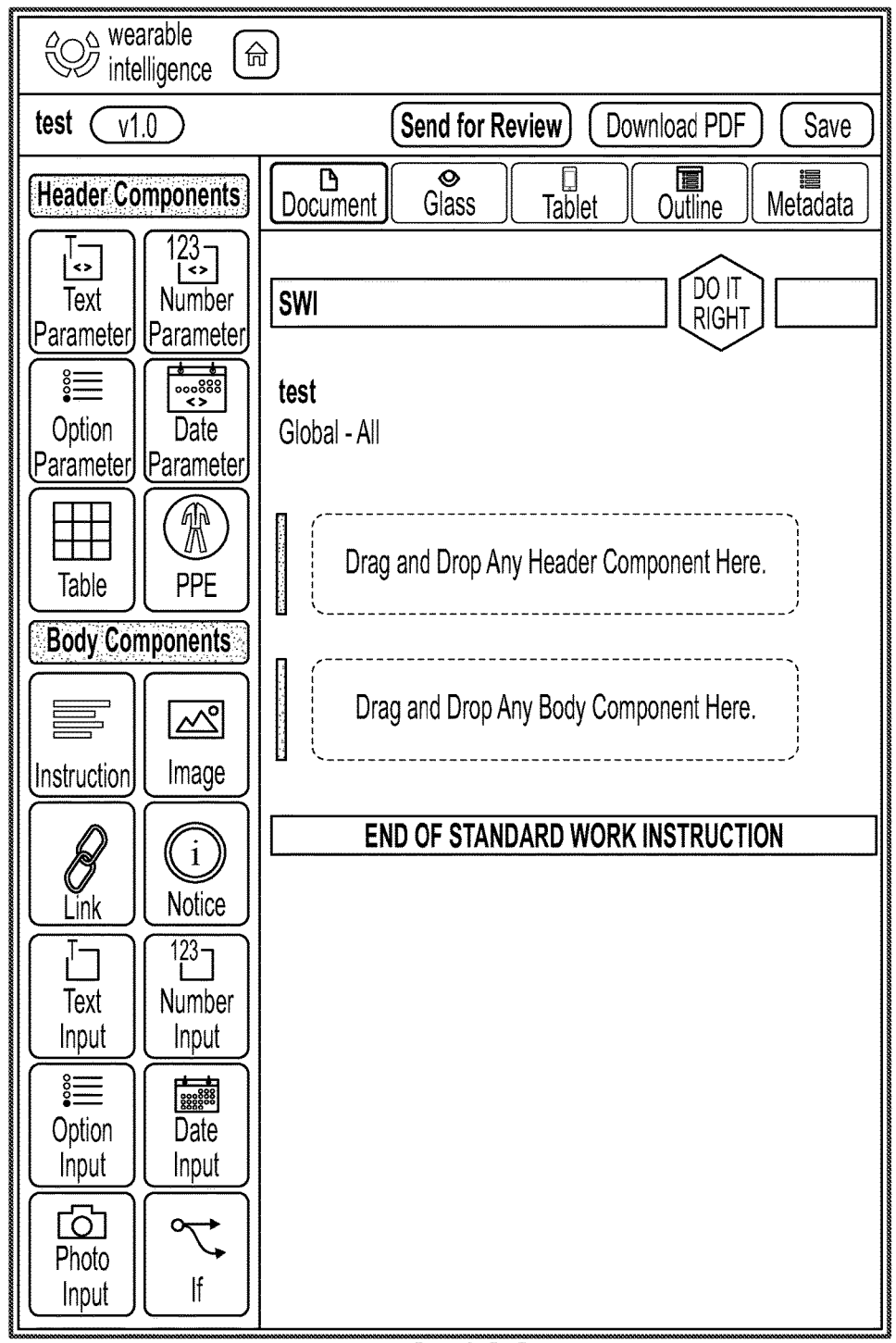

To create a procedure, a user can select a "new standard work" button on the front page dashboard of the authoring interface (see FIG. 18A) and input various configuration metadata entries (see FIG. 18B). The user is then redirected to a page displaying a blank procedure (see FIG. 18C).

Figure 18D:
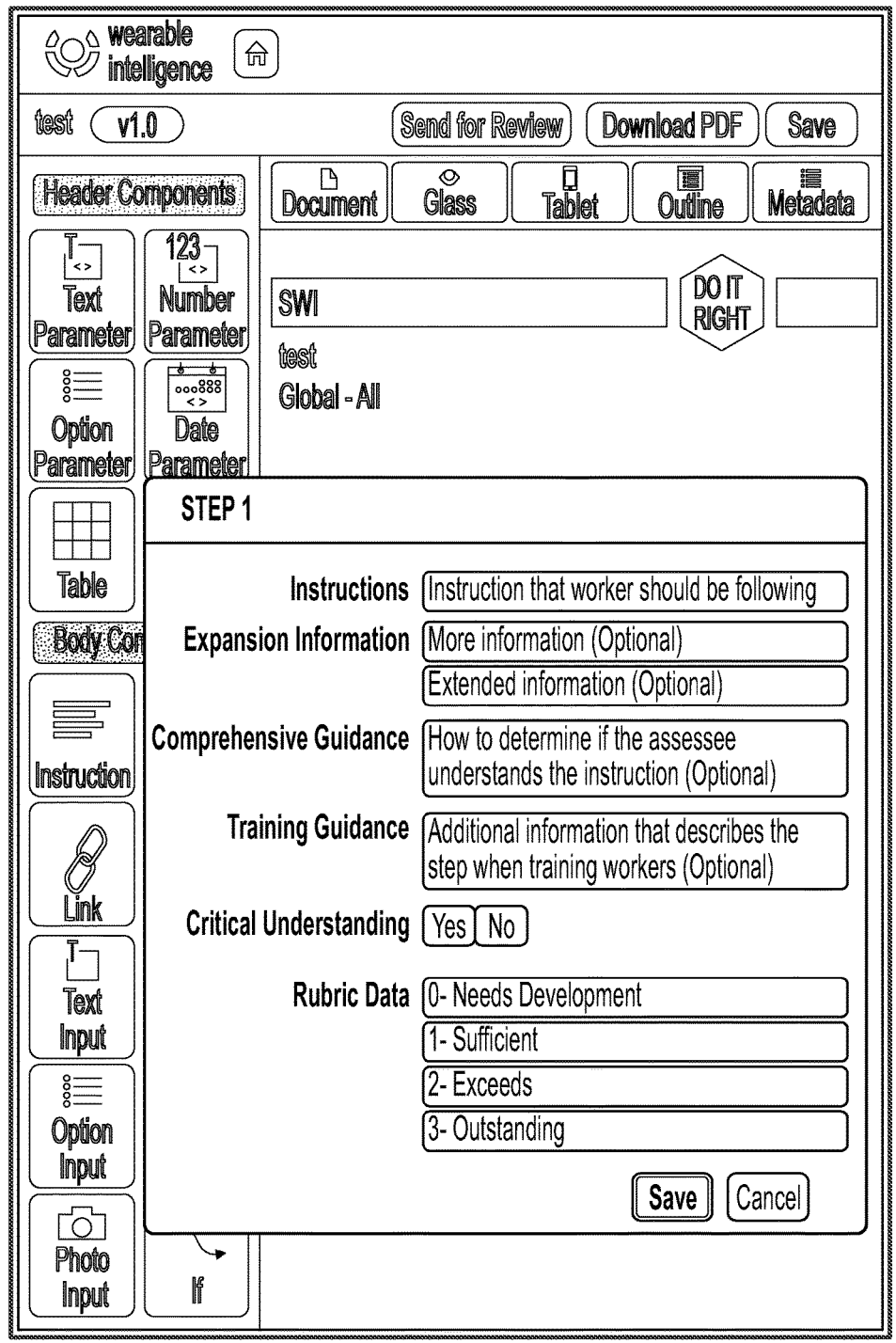

In the editing dashboard, there are two main active panels: the left panel contains the step palette, and the right panel contains the WYSWIG interface. To add a step to the new procedure, the user can drag one of the elements from the step palette on the left into an active area on the right. As the step is "dropped" into an active area, a modal dialogue appears that allows the user to input information about the step (see FIG. 18D).

Figure 19A:
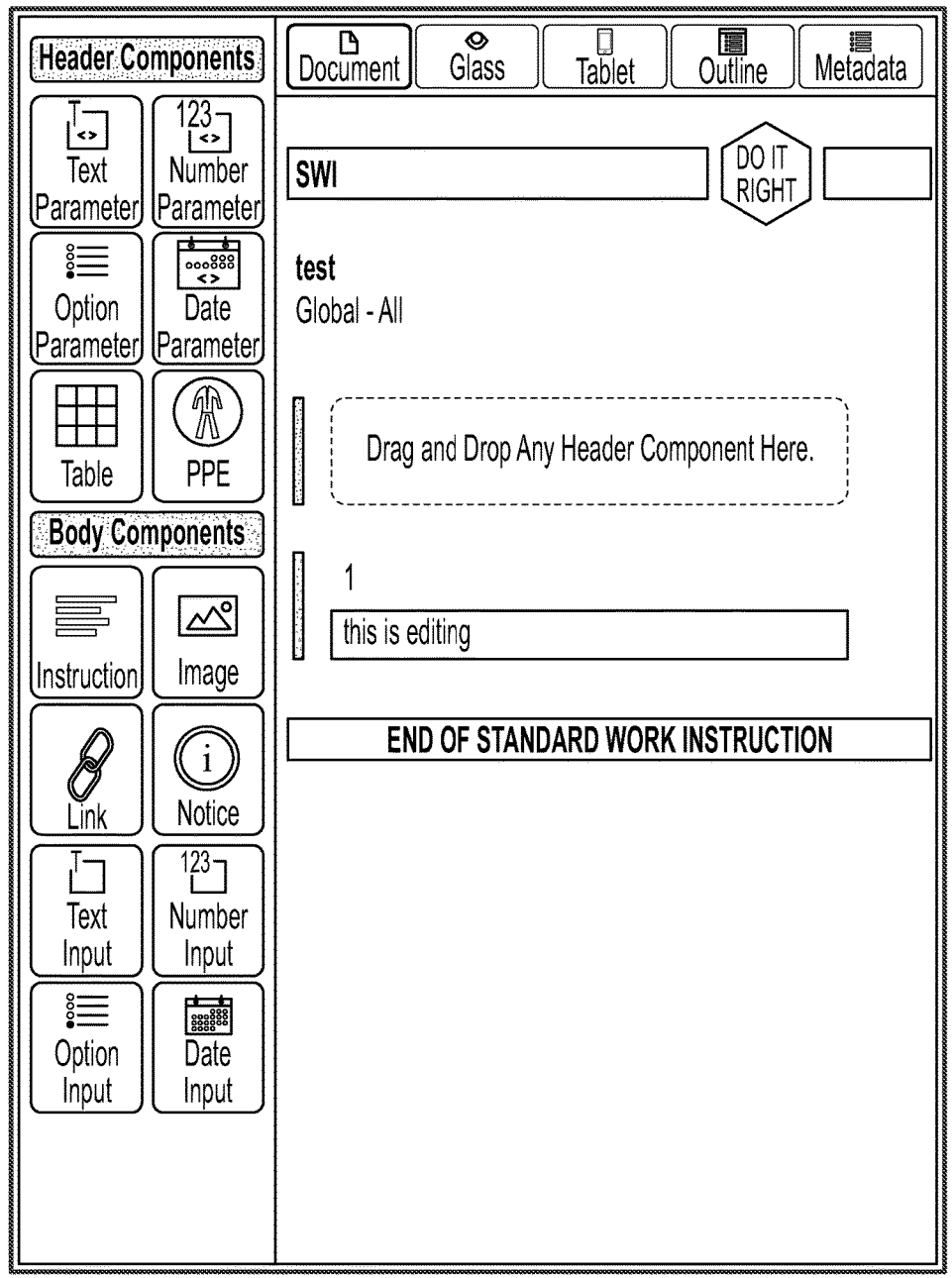
Figure 19B:
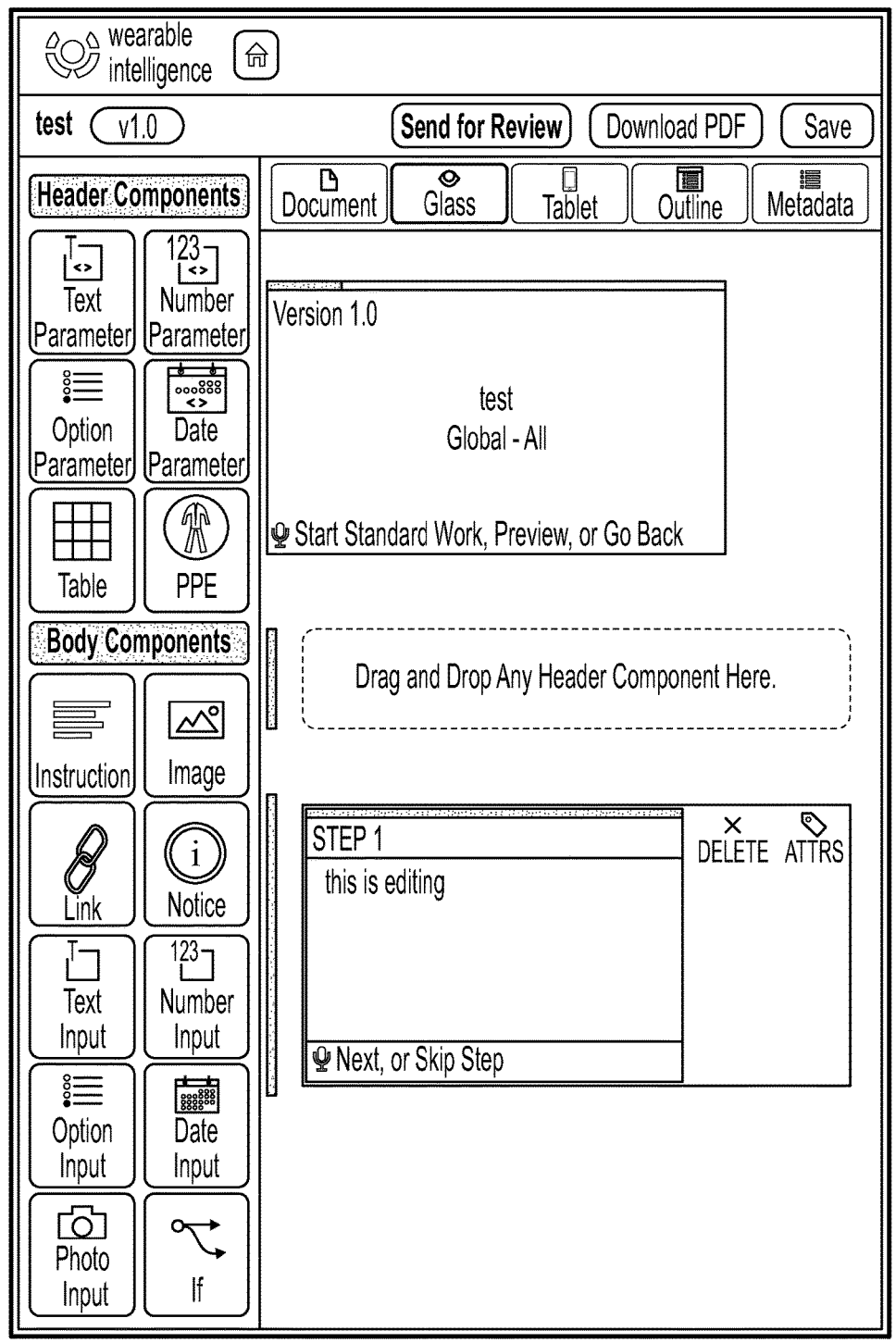
Figure 19C:
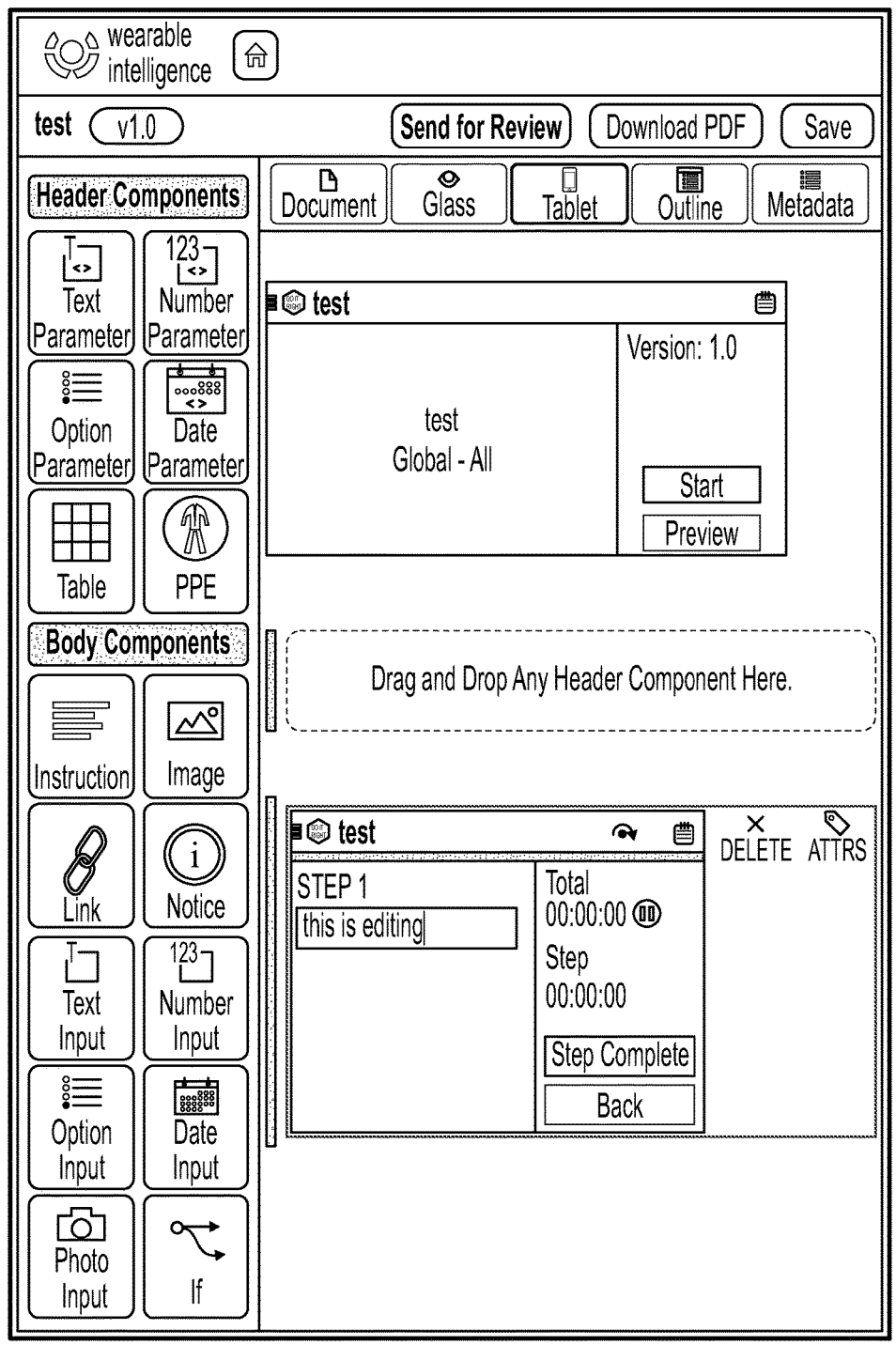

WYSIWYG editing is shown in FIGS. 19A-19C for this step in a few different views. The text "this is editing" is in a text field that is being edited during the screen capture. FIG. 19A depicts the document view; FIG. 19B, the wearable device view; and FIG. 19C, the tablet view.

The steps within the step palette are each constructed from step primitives, and represent steps in WIML. In the administrative construction panel, administrative users can construct steps from primitives and add these steps to the palette. Completed steps can be saved in a "step library" and used in different procedures. This allows common steps to be written once and run in multiple procedures where needed. Additionally, each procedure can load steps from this step library. Completed checklists can be combined into work sets that can be executed in series, executed using predetermined branching logic or executed "intelligently" where branching between procedures is determined via an customer provided software integration.

Standard Work Approval and Deployment

In one implementation, the authoring interface provides a dashboard to approve, version and deploy procedures across all execution platforms. The dashboard allows a procedural workflow author to configure the versioning system. The author can define the value of the initial version and can also define how the value changes on every version update. When a procedural workflow is created, it gets assigned the initial version value (e.g., 1.0), and its status is set to "Editing." The author can edit the procedure when it is in the "Editing" status.

Figure 20:
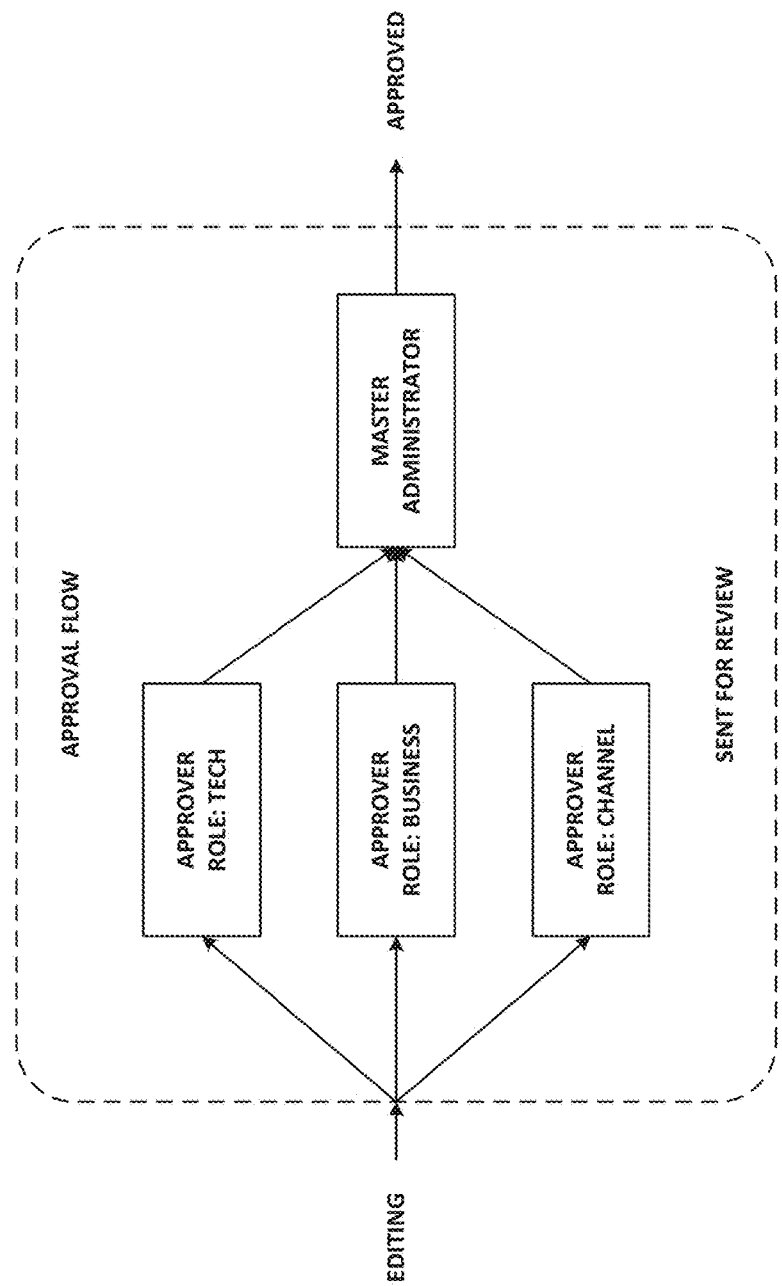
FIG. 20 depicts an example approval workflow for an authored procedural workflow.

Once satisfied with the changes made to a procedure, the procedural workflow author can send the procedure for review. This puts the procedure in a "Sent for Review" status and freezes it against edits until it goes through the approval process. The approval process is configurable, and can consist of multiple stages to be executed concurrently or sequentially. A sample approval flow is illustrated in FIG. 20. As shown, each stage is associated with a role. At each stage, an approver with the role corresponding to that stage can either approve or reject the procedure.

In some implementations, rejection at any stage removes the procedure from "Sent for Review" status and puts it back into the "Editing" status. The author of the procedure is notified of the same. When an approver rejects the procedure, the approver can be provided with the option to add comments explaining the action. The author of the workflow can refer to the comments, make corresponding changes to the procedure, and send it again for review.

If the procedural workflow successfully makes it through all (or at least the required) defined stages of the approval process, it proceeds to the "Approved" status. An approved workflow is ready to be deployed across all execution platforms. The workflow can be saved (e.g., as an XML-based file) and packaged into a zip archive along with accompanying media assets and uploaded to a procedural workflow storage server. Workflow execution platforms can periodically query the procedural workflow storage server for new procedures or version updates to existing workflows and, subsequently, new checklists can appear automatically on connected devices.

Intelligent Standard Work Scheduling

The execution of standard work allows a few ways for work to be "intelligently scheduled" for workers during both authoring and execution. Intelligent work scheduling is a way to enhance "bundles" of procedures that are executed in series by selecting correct branching logic, or removing duplicate work using built in primitives.

One way to intelligently schedule/execute standard work procedures is using the "do once" primitive within a step. This primitive allows steps to be "hidden" depending on the context of execution. Individual steps can appear in multiple different procedures (the user can load commonly used steps from a library of complete steps). These "library" steps can be tagged with a "do once" flag. During the execution of a workflow, if a step with a "do once" flag is encountered, the execution engine will check if an identifier associated with the step exists in a list of completed steps, indicating that the step has been completed in an earlier procedure within the set. If the identifier is found within the list, then the step is skipped because of its previous execution. If, on the other hand, the identifier is not found within the list, then the step is displayed normally, because it is the first time that the step is executed.

An example use case for the "do once" primitive in a step is in a work set that contains multiple procedures relating to machine maintenance. Procedures A and B are executed sequentially. Step 1 of both procedures A and B is a library step that instructs the executor to "Lock Out, Tag Out" for safety compliance. Both procedures A and B, when executed individually, require the "lock out, tag out" instruction but, if they are executed in sequence, the maintainer should already be "locked out, tagged out" during the execution of procedure B because they will have had completed that step in procedure A. Adding this primitive to the step allows the execution engine to not display the "log out, tag out" step in procedure B after it has been executed in procedure A, thus reducing redundant work.

Another way to schedule/execute standard work procedures is by creating standard work sets dynamically based on application programming interface (API) links to a workflow service. The API provides access to procedure libraries and execution data in real time. This allows a procedural workflow author to build software services that read data using the API and select which procedures to branch to given current conditions. This in essence allows the creation of "dynamic work sets," or dynamically created work sets that exist only in a current execution context and are assembled based on values determined in execution.

An example of this is a when a user begins a dynamic checklist starting with procedure A, which walks the user through changing the transmission fluid of an oil rig drill bit gear driver. Procedure A instructs the user to measure the specific gravity and temperature of the transmission fluid. At the end of procedure A, the dynamic set execution context makes a call to a dynamic work set generation engine, which can be provided by the workflow author organization, passing in certain data gathered in executing the procedure. The dynamic work set generation engine returns an identifier associated with a library procedure that can be executed given the gathered data from procedure A. The workflow then proceeds to execute the procedure selected by the dynamic work set generation engine.

Procedural Workflow Execution on End User Devices

The Director application allows for the execution of procedural workflows on end user devices such as desktops, laptops, tablets, and mobile devices via browser applications, as well as tablets, mobile devices, and wearable devices via native applications.

With respect to wearable devices (e.g., Google Glass®), various software enhancements provide user experience and navigation improvements. For example, a software-based component is included for passive voice listening and evaluating voice commands for navigation between screens. Rather than wait for a particular keyword or phrase (e.g., "OK Glass"), the component ignores/filters noise and listens for audio that sounds like spoken words. Recognized words can then be matched to navigation commands. As another example, sensors in the wearable device (e.g., gyroscope, accelerometer, etc.) can be used to determine head position and movement, allowing for head-scrolling recognition and navigation of views which exceed the physical size of the screen.

In one instance, interface screens, or "cards," can include titles or other text that has semantic value and can be included in the local and/or remote dictionary of the wearable device. Voice recognition can be used to detect when a title or other text associated with a card is spoken, and the card can be navigated to on command. Other commands associated with a card can also be executed on voice command, such as retrieving or sending data, capturing an image or video, and so on.

As another example, the wearable device can be paired with and controlled using a Bluetooth and/or near field communication (NFC) ring. Further, a peripheral projector can display a virtual keyboard that is paired to the wearable device and acts as an alternate means of input.

The Director application provides significant benefits over existing ad-hoc mobile workflow solutions, such as an increase in procedural adherence. By having a standardized and easy-to-use checklist, operators are far more likely to complete procedures as specified. In addition, the user experience is designed to be engaging rather than a burden on the field operator. Because many procedures and workflows are designed to increase safety, increased adherence also leads to fewer incidents or accidents. Operators failing to adhere to procedures can lead to costly downtime due to incorrect operation of equipment, etc. and, thus, reducing downtime has a tangible financial benefit.

Using the Director application a company can also easily maintain records that tasks were completed and protocols followed, with video and photo evidence. Further, unlike alternative solutions based on mobile phone or tablet hardware, the hands-free nature of the wearable headset provides for greater convenience (leaving both of the operator's hands free to do the job), is more robust (less chance of devices being dropped, lost or broken), and in situations requiring it the hands-free nature allows for sterile conditions to be maintained.

In one implementation, once authenticated on an end-user device, a user is presented with a dashboard that lists the standard work (procedural workflow(s)), filterable by one or a combination of options available in the metadata of that standard work. The status of each standard work is also displayed (e.g., Not Started, Aborted, Incomplete, Complete).

Upon selecting a standard work to execute, the Director application on the end user devices renders the WIML document of that standard work into viewable and/or actionable steps. The user can be initially presented with a preview of the steps that compose that standard work on a single screen in a scrollable view. From there, the user can continue on to execute the standard work, step by step.

There are several types of steps that a user can be presented with, as constructed using the authoring interface (described above). They can be viewable steps that display content such as text, zoomable images, video, audio, etc. There are also actionable steps that request input such as capturing images or video, scanning barcodes, alphanumeric text entry, selecting an option from a dropdown menu, etc. The actionable steps can also be skipped, provided that a reason for skipping the step is given.

Depending on the medium of execution, the steps may be presented or interacted with in different fashions. For example, on a wearable device such as Google Glass®, the primary means of input are voice commands and, due to the limited screen real estate, some presentable data may be hidden until triggered visible by a specific voice command. On the other hand, a desktop web browser can present more information at one time and can accept keyboard and mouse input.

In addition to user interface and experience changes across the mediums of execution, architectural changes can also exist. For example, a mobile device may need to queue posting data to a server to save on battery or until a stable network connection is established, whereas a desktop web browser that has more computational power and a persistent network connection can post data to the server as it comes in. Of note, the various execution platforms render and handle the WIML document in these various fashions but the document itself does not change; the same document can be used across these execution platforms.

In some implementations, a user can navigate forwards and/or backwards through the standard work, with the Director application recording a stack trace of the steps visited. The user is typically presented with the option to proceed to the next step or go back in the stack trace. Actionable steps can also contain branching logic which, depending on the input the user provides, can navigate the user to different steps of the standard work, though not necessarily in chronological order.

Actionable steps can be marked as gating or blocking, which will not allow the user to proceed until the requested action is completed. Actionable steps can also be assigned, expected, minimum, and/or maximum values. In the event that the user's input does not fit the bounds assigned, the standard work can proceed as defined in the WIML document. For example, the WIML document can require the standard work to ignore the invalid input and proceed to the next step, jump to a specified step, or abort and return to the dashboard.

Various metrics can be collected by the Director application, such as the time a user spends on each step. A user can also optionally choose to leave feedback on a step. At points throughout the standard work, the user can also has the option to abort the standard work and return to the dashboard, provided a reason for aborting is given. The user can also choose to see all of the input he or she has currently recorded.

Upon completion of the standard work, the user can be presented with a review of the steps and recorded values for those steps in a similar fashion to the preview of the steps the user initially saw when beginning execution of the standard work. Here, the user can also be given the option to provide feedback on the standard work as a whole. The data collected and the user actions performed can be recorded on a remote server connected to the end user device.

Report and Data Display

Figure 21A:
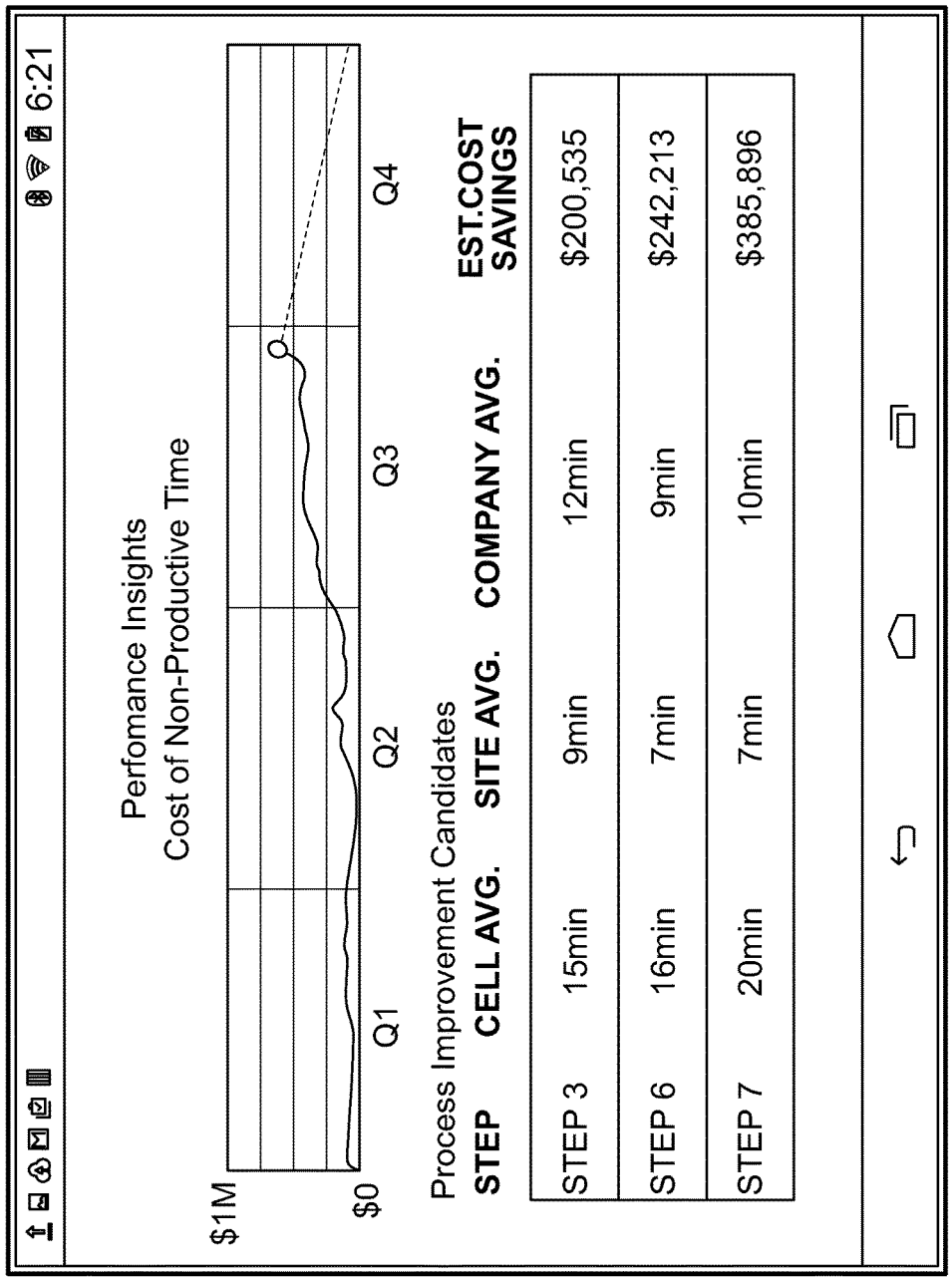
Figure 21B:
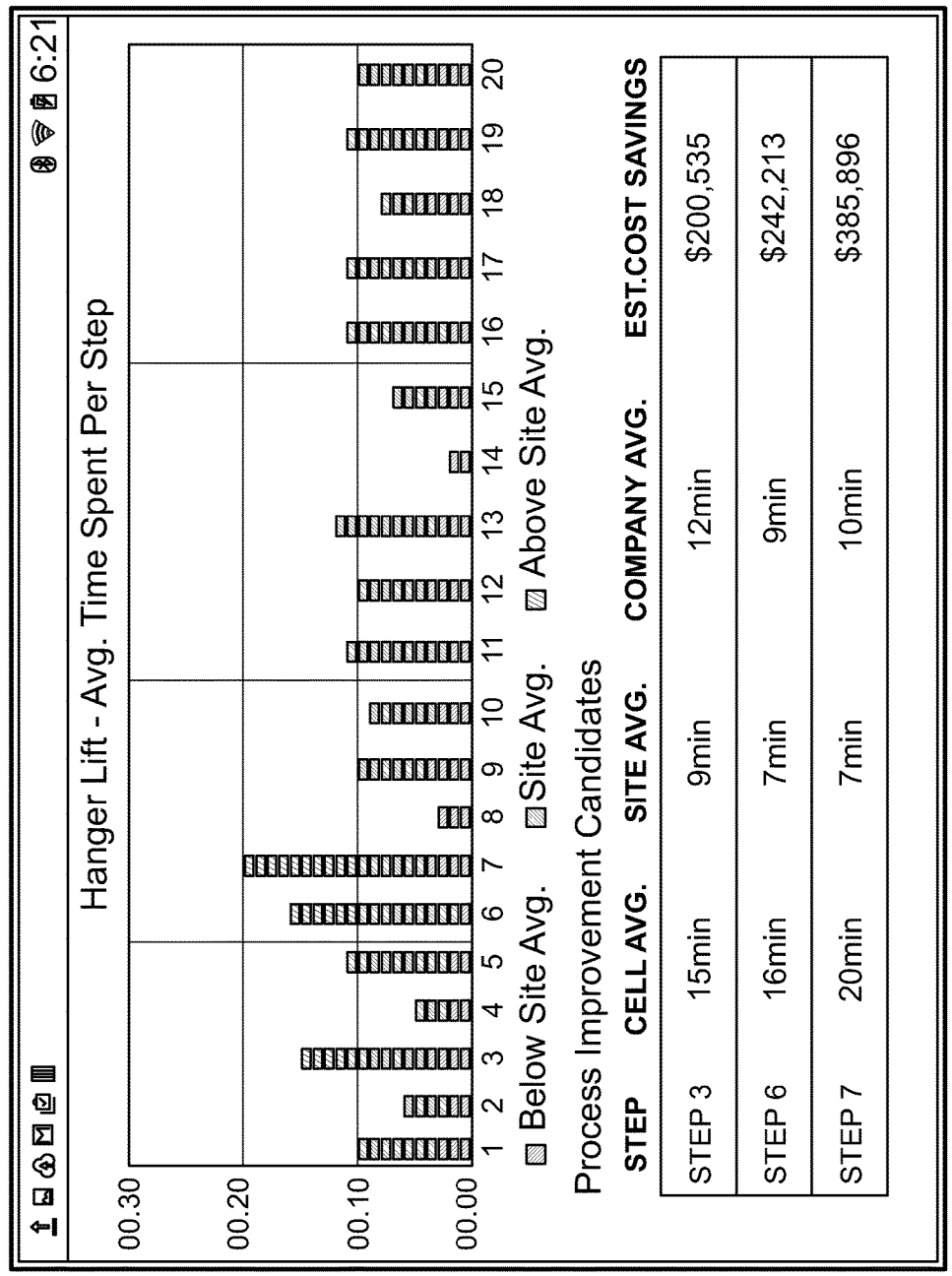

The execution of procedural workflows can result in the collection of data which can be further analyzed. Such data can include: average amount of time required to complete a standard procedure; average amount of time required to complete a step in a standard procedure; average amount of time taken by a particular person to complete a standard procedure; average amount of time taken by a particular person to complete a step in a standard procedure; average value generated by a step in a procedure (for example, average pressure recorded in a pipe); each of the foregoing but, instead of average value, the range of values and the total values; and completion or abortion percentage for a step or procedure. Other types of collected data are contemplated. FIGS. 21A and 21B depict an example graph and histogram, respectively, of trend data collected over multiple executions of a standard procedure. FIG. 21C depicts an example accounting of steps taken during the execution of a standard procedure.

Feedback Alerts

When executing a standard work procedure, an operator can submit feedback for each step in the procedure and for a procedure as a whole. The feedback can be submitted in a number of different ways, depending on the execution device being used. For example, feedback can be submitted using text entry, speech-to-text, and/or video. In the case of poor or no connectivity, the feedback can be saved locally on the end user device and then transmitted to a remote server when the device regains connectivity.

Feedback can be aggregated in various ways, for example, per step in a procedure, per procedure, per executor, per author, and/or per region. The aggregated feedback can be provided to the procedural workflow author via the dashboard and/or through email notifications whenever an executor submits feedback for a step/procedure that was created by the author. The author can then modify the procedure or take other appropriate action based on the feedback.

Avatar—Multimedia Communication and Remote Assistance

In one implementation, the present system provides multimedia communication and remote assistance functionality through an "Avatar" application executing on an end-user device and a corresponding application executing on a remotely connected system. The system enables a remote expert to communicate with an onsite worker, operator, or other user who has a wearable or other mobile device. The system incorporates live video and audio streaming as well as text, image, video, and audio messaging to establish communication.

In an industrial setting, the Avatar application enables experts to remotely supervise and guide field operators through complex procedures using two-way text and audio communications augmented by point-of-view perspective video. An in-field component of the Avatar application is controlled in a completely hands-free manner, allowing the operator to focus on the task at hand. The communication system can also interface with an existing corporate telecom infrastructure.

In a clinical setting, the Avatar application enables clinician experts to remotely supervise and guide other physicians, surgeons, nurses, and physician assistants through complex diagnoses or procedures using two-way text and audio communications augmented by point-of-view perspective video. The communication system can also interface with an existing clinical telecom infrastructure. For example, it can enable hands-free, dictated paging (of a resident, attending, nurse, tech) that is delivered via an existing pager network.

Figure 22:
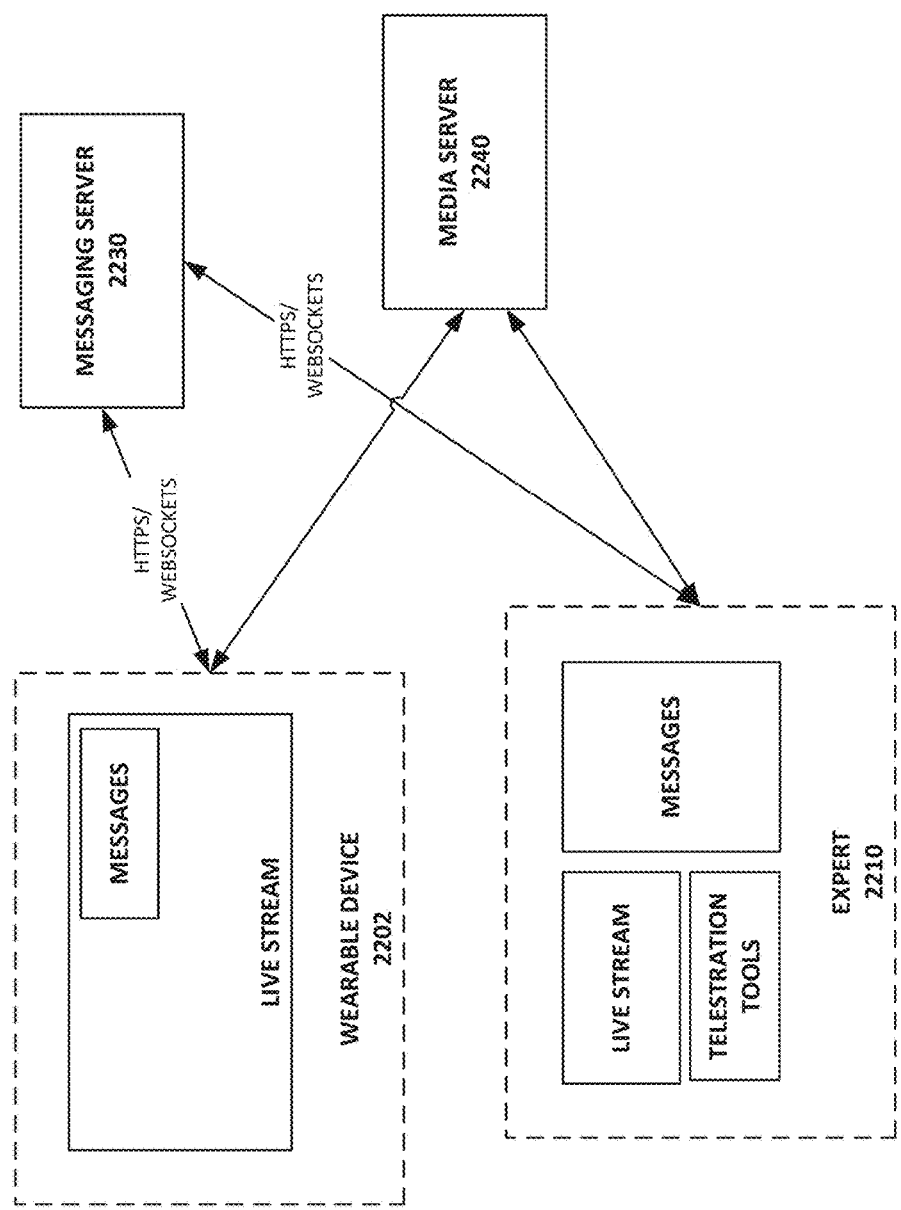
FIG. 22 depicts an example system architecture for a remote help system.

Referring to FIG. 22, a worker, using a wearable device 2202, can send live audio and/or video feeds over a network to Media Server 2240. Media Server 2240 can then relay the feeds to an expert 2210, who can be located anywhere in the world where network connectivity is available. The expert 2210 can use telestration tools on the live video feed including, but not limited to, adding free hand drawings to the live video feed, highlighting areas of the live video feed, adding text to areas of the live video feed, and highlighting objects on the live video feed. The expert 2210 can then send the telestrated images back to the wearable device 2202 of the onsite worker through Messaging Server 2230. The expert 2210 can also record his voice and send text messages to the worker through Messaging Server 2230 and, similarly, the work can send messages, recorded audio, images, and the like back to the expert 2210 through Messaging Server 2230.

Messaging Server 2230 guarantees delivery of a particular message at least once to the receiver (up to a certain amount of time), if it has acknowledged receiving the message to the sender regardless of whether the receiver is currently online. In low bandwidth situations where live video and audio are not possible, the expert 2210 and onsite worker can communicate through Messaging Server 2230 using messaging methods that use minimal amounts of bandwidth.

Figure 23A:
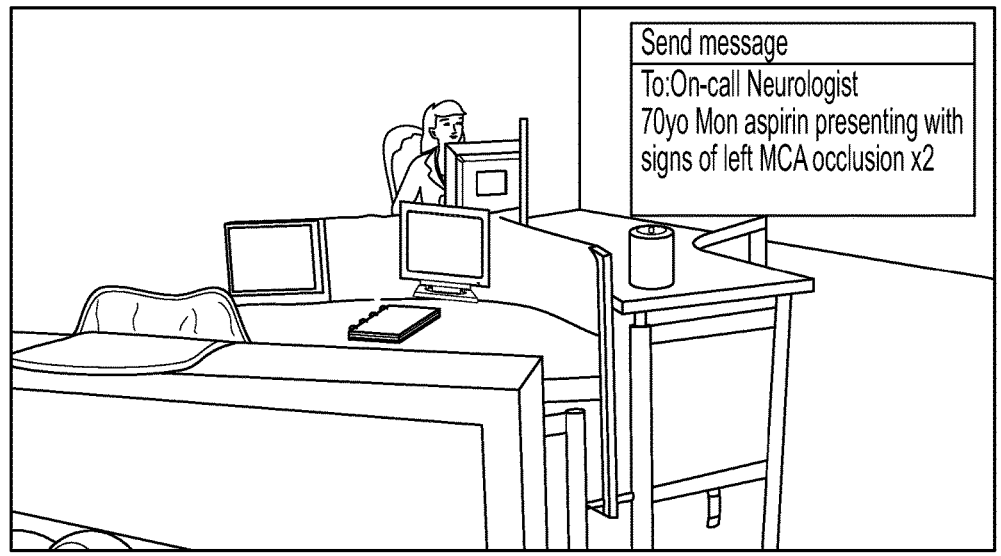
FIGS. 23A and 23B depict example end user displays in a remote help system.
Figure 23B:

Each worker can be equipped with a wearable headset, such as the Google Glass® or Microsoft HoloLens® wearable devices, thereby enabling the operators to stream their point-of-view perspective video and have a two-way text and audio conversation with experts while leaving their hands free to focus on the task-at-hand. The headsets can run custom software stacks to ensure that no data is transmitted to third-party servers and that the devices are secure within a particular organization's network. The communication system used by the headsets can also interface with mobile phones, tablets, pagers, computers, and other devices. It is not a requirement that both parties (worker and expert) are using a wearable headset. FIGS. 23A and 23B illustrate two-way text-based message communication while streaming a point-of-view perspective video using a wearable device.

The expert-facing (video-receiving) end of the interface can run on wearable hardware (including Google Glass® hardware) as well as standard mobile devices (phones, tablets, etc.) and/or desktop and laptop computers.

Expert Discovery

In various implementations, a worker can "discover" an expert that he would like to communicate with. For example, the worker can locate an expert using metadata associated with the expert, such as name, organization unit, role (e.g., Systems Engineer, Drilling Machine Expert, etc.), and/or geographical area (e.g., the expert closest to the worker, in city X, etc.). A company can also specify criteria by which an expert can be chosen based on an incoming request for a worker. For example, a company can filter incoming requests based on the specific business unit of the employee (i.e., match expert and worker from the same business unit). Experts can also be located using combinations of the foregoing criteria (e.g., Machine Drilling Expert in Houston).

The simple matching procedure described above works in many cases but, in order for a worker to connect with an expert that is well-suited to address their problem, an advanced matching procedure allows the worker to specify the problem in a few words before calling for an expert (e.g., stating that "the oil pump is not starting").

Figure 24A:
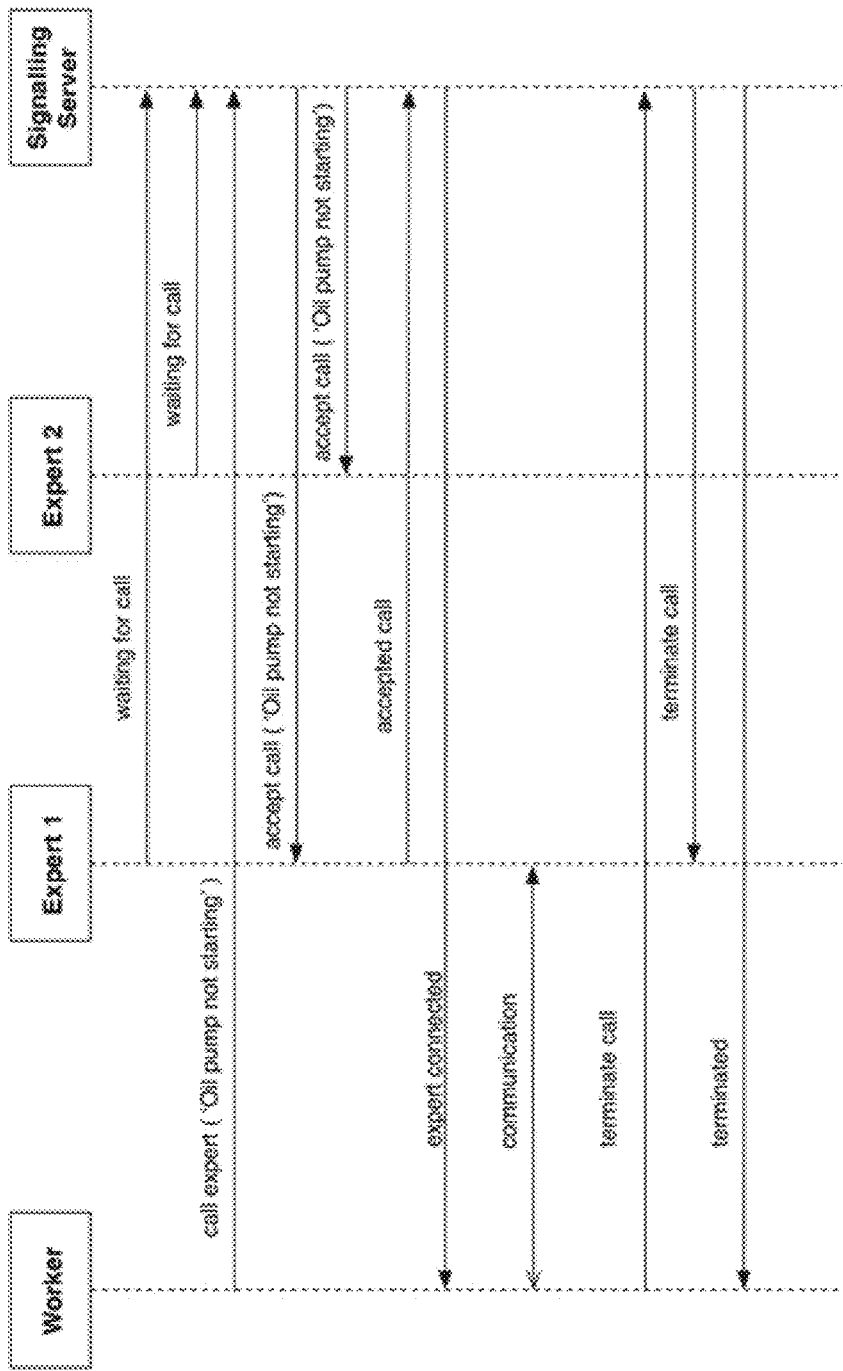
FIGS. 24A and 24B depict example processes for communicating with an expert in a remote help system.

Referring now to FIG. 24, a signaling server is responsible for call setup, management and tear down. Experts log into the remote help system and make themselves available to workers requesting assistance. When a worker needing help initiates a call to an expert, the signaling server can match the worker with the expert and set up the call. The signaling server can also perform teardown of the call once the call is terminated.

In a specific example, the signaling server performs a basic match with metadata to build a list of experts that can help a worker that has requested assistance. Once a group of experts is determined, the signaling server forwards the call acceptance request along with the problem statement mentioned by the worker to allow one or more experts to see the problem faced by the worker before they accept the call, thus allowing the right expert to help the worker. The system also allows the worker to record a small audio or video message instead of text, which the expert can also see before accepting the call.

The remote help system also allows an expert to respond to a worker in the event the worker does not receive help (e.g., no expert was available when the worker reported the problem). The issues provided by the worker in the form of text or a short video message can be made available to the expert when he logs in to the remote help system. The expert can then send a notification to the requesting worker to see if he or she is interested establishing a communication session to try and resolve the problem. In this case, the system can link the worker directly to the expert, thereby bypassing the selection process.

In some implementations, the remote help system allows workers to communicate with an expert over low bandwidth networks such as satellite via mobile devices. Due to high latency and low bandwidth it may not be possible to establish a live audio/video session between the two parties. When a live session is not possible, the worker can start the communication over a message channel where recorded audio, recorded video, image and text messages can be exchanged. This allows the expert to guide the worker even when network connection is not optimal.

Figure 24B:
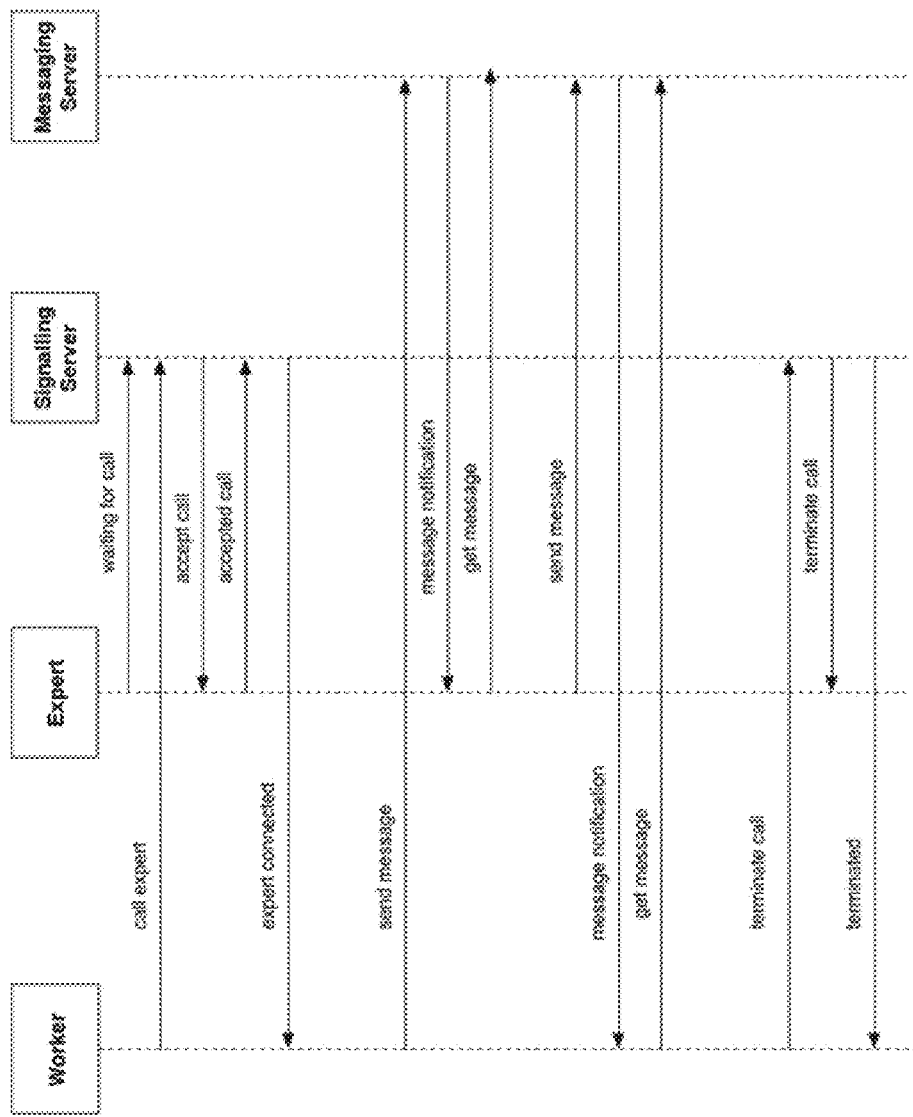

In this instance, referring to FIG. 24B, Messaging Server 2230 is responsible for relaying messages between the worker and expert. The messages can be video, audio, text and/or image-based. Since the remote help system is not live streaming, the quality of video and audio can be much higher compared to a live stream since they are recorded locally on the device and not compressed. The video and audio messages can be very short (e.g., a few seconds) in order to conserve bandwidth such that messages can be exchanged quickly. Messaging Server 2230 is also responsible for caching the messages so that if the worker or expert loses network connectivity intermittently they can reconnect to retrieve the messages.

Mentor—Video Training and Continuous Improvement

Figure 25A:
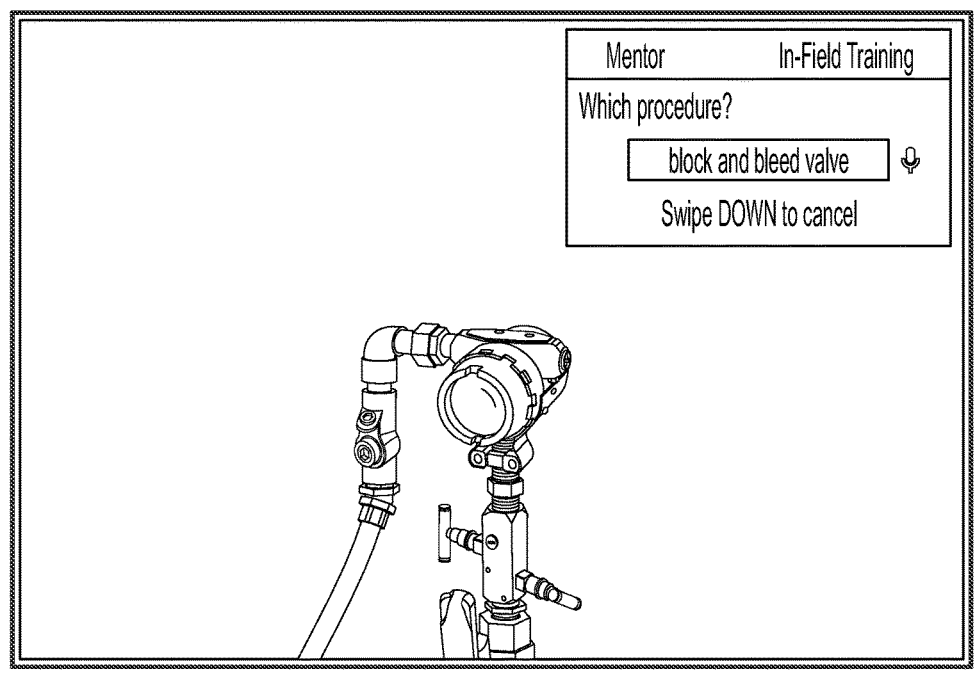
FIGS. 25A and 25B depict example end user displays in a mentoring system.
Figure 25B:
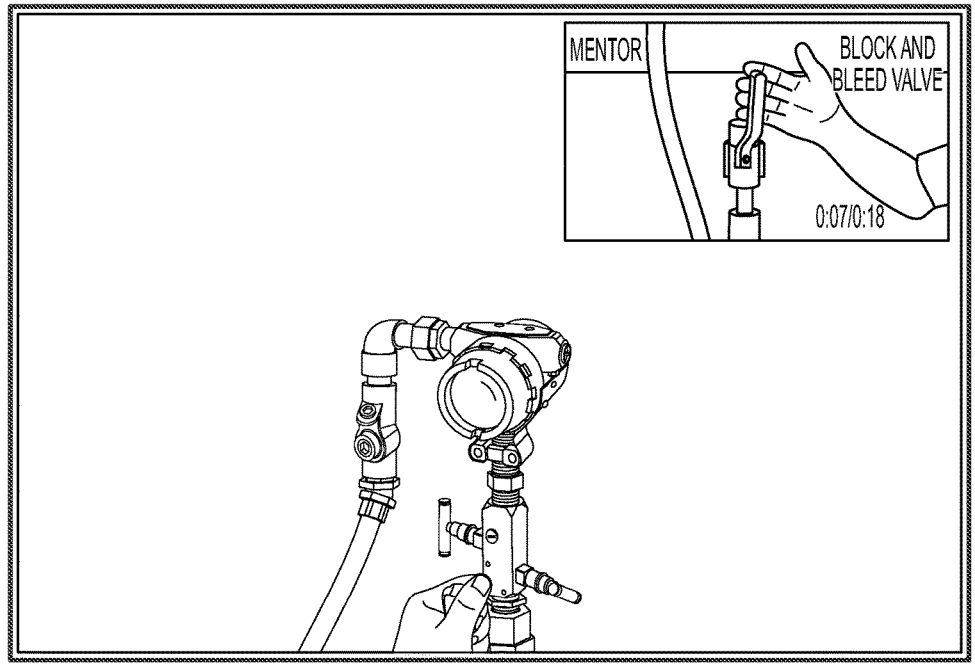

In one implementation, the present system includes a "Mentor" application that allows for video training to be recorded by and provided to an user's wearable device while the user is operating in the field. In an industrial setting, the Mentor application enables best-practice specialists to record point-of-view video in an unobtrusive, hands-free manner while completing complex operations. Other operators and trainees can review these videos in the field in a hands-free fashion in advance of performing critical steps. In a clinical setting, the Mentor application enables best-practice clinician specialists to record point-of-view video in an unobtrusive, hands-free manner while completing complex operations. Other clinicians, residents, and support staff can review these videos in the clinical environment in a hands-free fashion in advance of performing critical steps. FIGS. 25A and 25B depicts a best-practice procedure video requested and viewed in the field on a heads-up display.

Informant—Context-Aware Data and Alerts

Figure 26A:
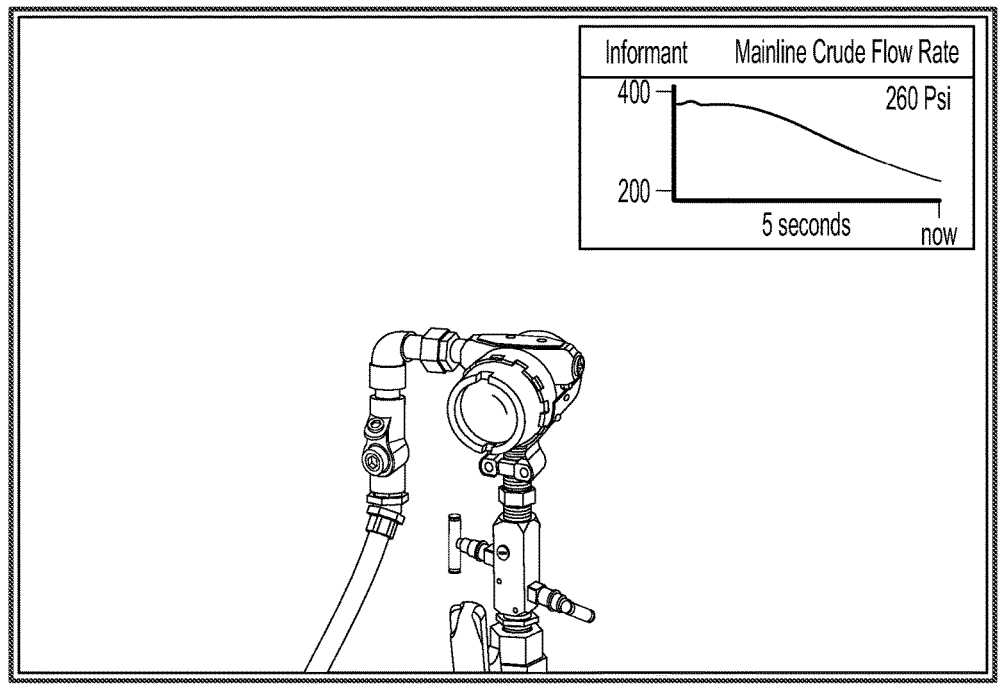
FIGS. 26A and 26B depict example end user displays in an information provision system.

In one implementation, the present system includes an "Informant" application that provides real-time data to the wearable device on an onsite worker. For example, in an industrial setting, the Informant application provides critical data in the operator's field of view to improve safety and situational awareness. Real-time telemetric data, along with critical alerts and notifications of error or exception conditions, is displayed in a hands-free unobtrusive manner in the field of view. The system is also able to respond to intelligent environment cues (including Bluetooth smart beacons) to display contextually-relevant data. In some instances, the data/alerts that are generated as a result of the wearable device detecting an object, condition, or other item are part of a primitive in a workflow or initiate a set of primitives in a new workflow. FIG. 26A depicts an example live telemetric report retrieved and streamed to a heads-up display in an industrial setting.

Figure 26B:
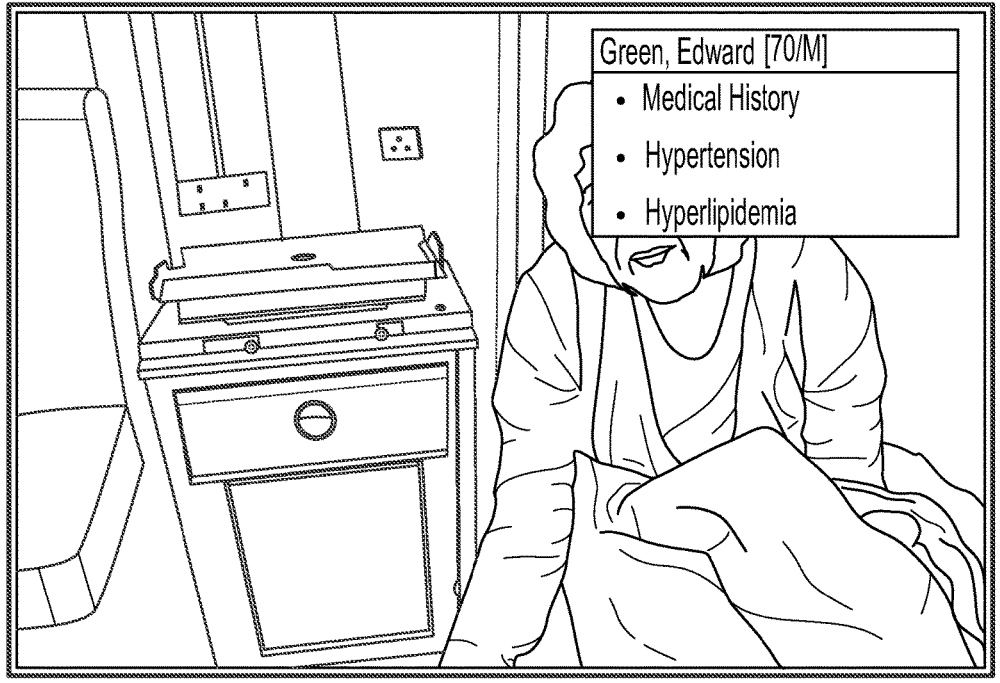

In a clinical setting, the Informant application provides data in the clinician's field of view to improve safety and situational awareness. Real-time telemetric data (including vitals streams), data pulled from the clinical systems like the Electronic Health Record, along with critical alerts and notifications of error or exception conditions, is displayed in a hands-free unobtrusive manner in the field of view. Data pulled from clinical systems can include, but is not limited to, patient lists (including room, patient name, chief complaint, resident assigned), labs, vitals, radiology data, provider lists (the resident, attending, nurse and tech assigned to this patient), medications, comments, and so on. The system can send push notifications to clinicians when new data arrives that is relevant to one of their patients (e.g., a new radiology result). The system is also able to respond to intelligent clinical environment cues (including Bluetooth smart beacons) to display contextually-relevant data. In some instances, the data/alerts that are generated as a result of the wearable device detecting an object, condition, or other item are part of a primitive in a workflow or initiate a set of primitives in a new workflow. FIG. 26B depicts example contextually-relevant health data retrieved and provided to a heads-up display in a clinical setting.

Remote Data Entry

In one implementation, the present system provides the ability for operators to record data into central systems while they are remote, mobile and on the move. For example, a doctor can dictate comments after examining a patient and have the comments immediately sent and stored in a central Electronic Health Record system. Similarly, a field operator can dictate information about equipment in the field and have the information sent back to a central server.

Materials and Inventory Management

Operators often need to track materials and equipment in the field. To avoid the cumbersome task of carrying around pen and paper, or running back and forth to a nearby computer, the present system can allow an operator to scan equipment barcodes and dictate relevant information using voice. This data can then be transmitted to a central inventory management server for tracking.

System Implementations

Implementations of the present system can use appropriate hardware or software; for example, the various applications executing on user devices and/or remote server(s) as described herein can execute on a systems capable of running an operating system such as the Microsoft Windows® operating systems, the Apple OS X® operating systems, the Apple iOS® platform, the Google Android™ platform, the Linux® operating system and other variants of UNIX® operating systems, and the like. The software described herein can be implemented on a general purpose computing device in the form of a computer including a processing unit, a system memory, and a system bus that couples various system components including the system memory to the processing unit.

Additionally or alternatively, some or all of the functionality described herein can be performed remotely, in the cloud, or via software-as-a-service. For example, as described above, certain functions can be performed on one or more servers or other devices that communicate with user devices over a network. The remote functionality can execute on server class computers that have sufficient memory, data storage, and processing power and that run a server class operating system (e.g., Oracle® Solaris®, GNU/Linux®, and the Microsoft® Windows® family of operating systems).

The system can include a plurality of software processing modules stored in a memory and executed on a processor. By way of illustration, the program modules can be in the form of one or more suitable programming languages, which are converted to machine language or object code to allow the processor or processors to execute the instructions. The software can be in the form of a standalone application, implemented in a suitable programming language or framework.

Method steps of the techniques described herein can be performed by one or more programmable processors executing one or more computer programs to perform functions by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors. Generally, a processor receives instructions and data from a read-only memory or a random access memory or both. The essential elements of a computer are a processor for executing instructions and one or more memory devices for storing instructions and data. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. One or more memories can store media assets (e.g., audio, video, graphics, interface elements, and/or other media files), configuration files, and/or instructions that, when executed by a processor, form the modules, engines, and other components described herein and perform the functionality associated with the components. The processor and the memory can be supplemented by, or incorporated in special purpose logic circuitry.

In some implementations, a user device includes a web browser, native application, or both, that facilitates execution of the functionality described herein. A web browser allows the device to request a web page or other program, applet, document, or resource (e.g., from a remote server, such as a web server) with an HTTP request. One example of a web page is a data file that includes computer executable or interpretable information, graphics, sound, text, and/or video, that can be displayed, executed, played, processed, streamed, and/or stored and that can contain links, or pointers, to other web pages. In one implementation, a user of the user device manually requests a resource from a server. Alternatively, the user device automatically makes requests with a browser application. Examples of commercially available web browser software include Microsoft® Internet Explorer®, Mozilla® Firefox®, and Apple® Safari®.

In other implementations, the user device includes client software that provides for the implementation and execution of the features described herein. The client software can be implemented in various forms, for example, it can be in the form of a native application, web page, widget, and/or Java, JavaScript, .Net, Silverlight, Flash, and/or other applet or plug-in that is downloaded to the device and runs in conjunction with a web browser. The client software and the web browser can be part of a single client-server interface; for example, the client software can be implemented as a plug-in to the web browser or to another framework or operating system. Other suitable client software architecture, including but not limited to widget frameworks and applet technology can also be employed with the client software.

A communications network can connect user devices with one or more servers or devices. The communication can take place over media such as standard telephone lines, LAN or WAN links (e.g., T1, T3, 56kb, X.25), broadband connections (ISDN, Frame Relay, ATM), wireless links (802.11 (Wi-Fi), Bluetooth, GSM, CDMA, etc.), for example. Other communication media are contemplated. The network can carry TCP/IP protocol communications, and HTTP/HTTPS requests made by a web browser, and the connection between the client device and servers can be communicated over such TCP/IP networks. Other communication protocols are contemplated.

The system can also be practiced in distributed computing environments where tasks are performed by remote processing devices that are linked through a communications network. In a distributed computing environment, program modules can be located in both local and remote computer storage media including memory storage devices. Other types of system hardware and software than that described herein can also be used, depending on the capacity of the device and the amount of required data processing capability. The system can also be implemented on one or more virtual machines executing virtualized operating systems such as those mentioned above, and that operate on one or more computers having hardware such as that described herein.

It should also be noted that implementations of the systems and methods can be provided as one or more computer-readable programs embodied on or in one or more articles of manufacture. The program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

Appendix A—Wearable Intelligence Markup Language (WIML) (XML-Format)

Wearable Intelligence Markup Language (WIML) is an XML-based markup language used to define structured information for display on wearable technology (e.g., Google Glass®). WIML can support both JSON- and XML-based representations. The examples below are directed toward structured workflows and checklists for industrial workers, although other purposes are contemplated.

Header

WIML documents that describe a procedure can begin with a header of the form:

```
<?xml version="1.0" encoding="UTF-8"?>
<wi:procedure xmlns:wi="http://wearableintelligence.com/wiml">
...procedure definition...
</wi:procedure>
```

Metadata

A procedure's metadata section provides information about the procedure's author, approver, date and version as shown in the example below.

```
<wi:metadata>
    <wi:version>1.0</wi:version>
    <wi:date>2013-09-11T12:44:54-05:00</wi:date>
    <wi:author>John Smith</wi:author>
    <wi:approver>Kelly Jones</wi:approver>
</wi:metadata>
```

Overview

The overview section describes the procedure's name and number, its objective, and any preconditions necessary before beginning the procedure.

```
<wi:overview>
    <wi:procedureNumber>1.23</wi:procedureNumber>
    <wi:name>Sample Procedure</wi:name>
    <wi:objective>This procedure is intended for maintenance
    technicians working on the XYZ widget. The instructions guide the
    technician through the initial stage of replacing a flux capacitor.
    </wi:objective>
    <wi:precondition>
     <wi:list>
       <wi:title>Before Starting</wi:title>
       <wi:item>Appropriate personal safety equipment must be
       used at all times</wi:item>
       <wi:item>Read the material safety data sheet for the flux
    capacitor before starting this procedure</wi:item>
     </wi:list>
    </wi:precondition>
</wi:overview>
```

Section

A procedure can be broken up into a series of sections in order to help with organization or to facilitate branching logic. A section has a title, and can have a list of required safety equipment, as well as set of steps.

```
<wi:section sectionID="s1">
    <wi:title>
        <wi:text>Removing the Flux Capacitor</wi:text>
    </wi:title>
    <wi:equipment>
        <wi:list>
            <wi:item>
                <wi:text>Safety Goggles</wi:text>
                <wi:image src="files/safety_goggles.png" />
            </wi:item>
            <wi:item>
                <wi:text>Gloves</wi:text>
                <wi:image src="files/gloves.png" />
            </wi:item>
        </wi:list>
    </wi:equipment>
    ...steps...
</wi:section>
```

Table

For complex lists of equipment/parts, the data can be displayed in a table instead.

```
<wi:equipment>
    <wi:table>
        <wi:title>Equipment List</wi:title>
        <wi:columnLabels>
            <wi:columnLabel>Part Number</wi:columnLabel>
            <wi:columnLabel>Description</wi:columnLabel>
```

-continued

```
        <wi:columnLabel>InTouch</wi:columnLabel>
    </wi:columnLabels>
    <wi:row>
        <wi:cell>S-279118</wi:cell>
        <wi:cell>Normal Flow Navigation Sub IWOB</wi:cell>
        <wi:cell>3922290</wi:cell>
    </wi:row>
    ...additional rows...
    </wi:table>
</wi:equipment>
```

Steps

The core unit of a procedure is a step. Steps can contain text, images, video and other elements. There are different types of steps (described below) depending on whether an instruction simply needs to be presented or input is required. Additional complex types of steps (such as multi-party collaboration) can be added.

Manual Step

A manual step display an individual step that needs to be performed by the worker completing this procedure. It is simply a descriptive step, with the only option being to advance to the next step or the previous step.

```
<wi:manualStep stepID="step1_2">
    <wi:number>1.2</wi:number>
    <wi:text>Install Shock Sleeve (5.1" or 5.9") if not already
installed</wi:text>
    <wi:image src="2.22_telescope_kitting_files/5_1shock.png"
        caption="5.1″ Shock Sleeve" />
</wi:manualStep>
```

Input Step

This type of step requires the worker to input some data. This may be one or more of text, photo or video. The value is stored in a variable that can be referenced elsewhere in the procedure, and will be accessible on the server.

```
<wi:inputStep stepID="step1_1">
    <wi:number>1.1</wi:number>
    <wi:text>Record S/N</wi:text>
    <wi:info infoType="note">As per recommendation, this should be
stamped on the endcap</wi:info>
    <wi:inputField variable="sn" dataType="numeric"
        inputMethod="text, photo" />
</wi:inputStep>
```

Verify Step

This type of step requires the worker to explicitly verify a piece of information and record a pass or fail value. The boolean result will be stored in the specified variable so that it can be referenced elsewhere in the procedure, and will be accessible on the server.

```
<wi:verify Step stepID="step5_18" variable="axial_loading">
    <wi:number>5.18</wi:number>
    <wi:text>Verify 5.9" Bore Axial Loading Device is 14.8
inches ±0.03</wi:text>
</wi:verifyStep>
```

Branching Logic

To facilitate procedures that must branch based on certain results, WIML supports simple branching logic as shown below. Branching is based on the value of a variable (defined by an input or verify step as above), and causes execution to jump to a specified step or section.

```
<wi:branch>
    <wi:condition variable="axial_loading" condition="equals"
        value="true" goto="s3" />
    <wi:condition variable="axial_loading" condition="equals"
        value="false" goto="s4" />
</wi:branch>
```

If execution should simply jump to a different location (no branching logic), the following can be used to jump to a specified section or step.

`<wi:goto reference="step4_9"/>`

Lastly, if the procedure should terminate at this point, the following can be used (along with specifying an overall result). If execution reaches the end of the procedure, it will exit with value "success".

`<wi:exit result="fail"/>`

Appendix B—Wearable Intelligence Markup Language (WIML) (JSON Format)

As mentioned in the overview in Appendix A, WIML can be expressed in either XML or JSON. For clarity, the XML examples from that Appendix are repeated here in JSON format.

Header

```
{
    "wi:procedure": {
        "-xmlns:wi": "http://wearableintelligence.com/wiml",
        ...procedure definition...
    }
}
```

Metadata

```
"wi:metadata": {
    "wi:version": "1.0",
    "wi:date": "2013-09-11T12:44:54-05:00",
    "wi:author": "John Smith",
    "wi:approver": "Kelly Jones"
}
```

Overview

```
"wi:overview": {
    "wi:procedureNumber": "1.23",
    "wi:name": "Sample Procedure",
    "wi:objective": "This procedure is intended for maintenance
technicians working on the XYZ widget. The instructions guide the
technician through the initial stage of replacing a flux capacitor.
",
    "wi:precondition": {
        "wi:list": {
            "wi:title": "Before Starting",
            "wi:item": [
                "Appropriate personal safety equipment must be used
                at all times",
                "Read the material safety data sheet for the flux
                capacitor before starting this procedure"
            ]
        }
    }
}
```

Section

```
"wi:section": {
    "-sectionID": "s1",
    "wi:title": { "wi:text": "Removing the Flux Capacitor" },
    "wi:equipment": {
        "wi:list": {
```

Table

```
"wi:item": [
    {
        "wi:text": "Safety Goggles",
        "wi:image": { "-src": "files/safety_goggles.png" }
    },
    {
        "wi:text": "Gloves",
        "wi:image": { "-src": "files/gloves.png" }
    }
  ]
 }
...steps...
}
```

Table

```
"wi:equipment": {
    "wi:table": {
        "wi:title": "Equipment List",
        "wi:columnLabels": {
            "wi:columnLabel": [
                "Part Number",
                "Description",
                "InTouch"
            ]
        },
        "wi:row": [
            {
                "wi:cell": [
                    "S-279118",
                    "Normal Flow Navigation Sub IWOB",
                    "3922290"
                ]
            },
            ...additional rows...
        ]
    }
}
```

Manual Step

```
"wi:manualStep": {
    "-stepID": "step1_2",
    "wi:number": "1.2",
    "wi:text": "Install Shock Sleeve (5.1" or 5.9") if not already installed",
    "wi:image": {
        "-src": "2.22_telescope_kitting_files/5_1shock.png",
        "-caption": "5.1\" Shock Sleeve"
    }
}
```

Input Step

```
"wi:inputStep": {
    "-stepID": "step1_1",
    "wi:number": "1.1",
    "wi:text": "Record S/N",
    "wi:info": {
        "-infoType": "note",
        "#text": "As per recommendation, this should be stamped on the endcap"
    },
    "wi:inputField": {
        "-variable": "sn",
        "-dataType": "numeric",
        "-inputMethod": "text, photo"
    }
}
```

Verify Step

```
"wi:verifyStep": {
    "-stepID": "step5_18",
    "-variable": "axial_loading",
    "wi:number": "5.18",
    "wi:text": "Verify 5.9\" Bore Axial Loading Device is 14.8 inches ±0.03"
}
```

Branching Logic

```
"wi:branch": {
    "wi:condition": [
        {
            "-variable": "axial_loading",
            "-condition": "equals",
            "-value": "true",
            "-goto": "s3"
        },
        {
            "-variable": "axial_loading",
            "-condition": "equals",
            "-value": "false",
            "-goto": "s4"
        }
    ]
}
"wi:goto": { "-reference": "step4_9" }
"wi:exit": { "-result": "fail" }
```

The terms and expressions employed herein are used as terms and expressions of description and not of limitation, and there is no intention, in the use of such terms and expressions, of excluding any equivalents of the features shown and described or portions thereof. In addition, having described certain implementations in the present disclosure, it will be apparent to those of ordinary skill in the art that other implementations incorporating the concepts disclosed herein can be used without departing from the spirit and scope of the invention. The features and functions of the various implementations can be arranged in various combinations and permutations, and all are considered to be within the scope of the disclosed invention. Accordingly, the described implementations are to be considered in all respects as illustrative and not restrictive. The configurations, materials, and dimensions described herein are also intended as illustrative and in no way limiting. Similarly, although physical explanations have been provided for explanatory purposes, there is no intent to be bound by any particular theory or mechanism, or to limit the claims in accordance therewith.

What is claimed is:

1. A method performed by a computing device, the method comprising:
encrypting information comprising a secret and a public key of the computing device using a public key of a remote system;
sending the encrypted information to the remote system;
receiving a response to the encrypted information from the remote system and decrypting the response using a private key of the computing device;
determining at a first time that the decrypted response matches the secret and based thereon:
verifying that the computing device is connected to a first network;
verifying that the computing device is located within a first geofence;

verifying that an environment of the computing device has not been altered in an unauthorized manner by determining whether the remote system is legitimate, wherein determining whether the remote system is legitimate comprises measuring data packet round trip time to determine whether a distance between the computing device and the remote system indicates that the computing device and the remote system are within a same geofence; and determining at a second time following the first time that the computing device is not connected to the first network or is not within the first geofence, and based thereon, performing one or more of: erasing application data stored on the computing device and erasing an application stored on the computing device.

2. The method of claim 1, further comprising determining that a location of the computing device has changed.

3. The method of claim 1 wherein determining at the second time further comprises determining that the computing device is connected to a second network wherein the second is not an approved network.

4. The method of claim 1 wherein the secret is a random number.

5. The method of claim 1 wherein the computing device is a wearable computing device.

6. The method of claim 1 wherein verifying that the computing device is connected to a first network comprises verifying that a service set identifier (SSID) of a network that the computing device is connected to matches an SSID for the first network.

7. A system comprising:
one or more computing devices programmed to perform operations comprising:
encrypting information comprising a secret and a public key of the computing device using a public key of a remote system;
sending the encrypted information to the remote system;
receiving a response to the encrypted information from the remote system and decrypting the response using a private key of the computing device;
determining at a first time that the decrypted response matches the secret and based thereon:
verifying that the computing device is connected to a first network;
verifying that the computing device is located within a first geofence;
verifying that an environment of the computing device has not been altered in an unauthorized manner by determining whether the remote system is legitimate, wherein determining whether the remote system is legitimate comprises measuring data packet round trip times to determine whether a distance between the computing device and the remote system indicates that the computing device and the remote system are within a same geofence; and determining at a second time following the first time that the computing device is not connected to the first network or is not within the first geofence, and based thereon, performing one or more of: erasing application data stored on the computing device and erasing an application stored on the computing device.

8. The system of claim 7, wherein the operations further comprise determining that a location of the computing device has changed.

9. The system of claim 7 wherein determining at the second time further comprises determining that the computing device is connected to a second network wherein the second is not an approved network.

10. The system of claim 7 wherein the secret is a random number.

11. The system of claim 7 wherein the computing device is a wearable computing device.

12. The system of claim 7 wherein verifying that the computing device is connected to a first network comprises verifying that a service set identifier (SSID) of a network that the computing device is connected to matches an SSID for the first network.

* * * * *